United States Patent
Solarz

(10) Patent No.: US 9,519,033 B2
(45) Date of Patent: *Dec. 13, 2016

(54) HIGH THROUGHPUT HOT TESTING METHOD AND SYSTEM FOR HIGH-BRIGHTNESS LIGHT-EMITTING DIODES

(71) Applicant: KLA-Tencor Corporation, Milpitas, CA (US)

(72) Inventor: Richard W. Solarz, Danville, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 14/589,728

(22) Filed: Jan. 5, 2015

(65) Prior Publication Data

US 2015/0123667 A1 May 7, 2015

Related U.S. Application Data

(63) Continuation of application No. 13/673,947, filed on Nov. 9, 2012, now Pat. No. 8,927,944.

(Continued)

(51) Int. Cl.
*G01R 31/44* (2006.01)
*H05B 33/10* (2006.01)
(Continued)

(52) U.S. Cl.
CPC .............. *G01R 31/44* (2013.01); *G01N 21/66* (2013.01); *G01N 21/71* (2013.01); *H01L 33/32* (2013.01); *H01L 33/44* (2013.01); *H05B 33/10* (2013.01)

(58) Field of Classification Search
CPC ..... G01R 31/44; H05B 33/10; G01N 21/6428; G01N 21/64; G01N 21/6408; G01N 21/645; G01N 2021/6421; G01J 3/4406; G01J 3/10; G01J 1/58; G01J 3/02; G01J 3/44; G01J 3/2803; G01J 3/36; G01J 3/0254; G01J 1/04; G01J 3/28; G01J 3/42; G01J 2001/4252; G02B 2207/113; H01L 2924/00; H01L 2924/00012; H01L 2224/48247; H01L 27/14692; H01L 21/02458

See application file for complete search history.

(56) References Cited

U.S. PATENT DOCUMENTS 7,301,274 B2 11/2007 Tanaka et al.
8,384,105 B2 * 2/2013 Tetz ...................... H01L 33/507
257/88

(Continued)

FOREIGN PATENT DOCUMENTS

CN 101968533 2/2011
CN 102072783 A 5/2011

(Continued)

OTHER PUBLICATIONS

Ansi, "Specifications for the Chromaticity of Solid State Lighting Products", ANSI_NEMA_ANSLG C78.377-2008, American National Standard Lighting Group, Jan. 9, 2008, 19 pgs.

(Continued)

*Primary Examiner* — Tarifur Chowdhury
*Assistant Examiner* — Mohamed K Amara
(74) *Attorney, Agent, or Firm* — Bever, Hoffman & Harms, LLP

(57) ABSTRACT

A method of performing a hot test of a packaged phosphor converted light-emitting diode (pc-LED) includes selectively heating portions of the phosphor layer using a laser to provide a predetermined temperature gradient in the phosphor layer. The selective heating can directly heat the silicone in a silicone-based phosphor layer, or directly heat the active ion(s) of the phosphor in a Lumiramic™-based (Continued)

phosphor or even the active ion(s) of a silicone-based phosphor layer. A current is applied to the InGaN film to establish a predetermined temperature at the InGaN film junction, the film junction being adjacent to the phosphor layer. Photometric measurements are performed on the LED after the selective heating and during the applied electroluminescent current. This method quickly establishes the temperatures and temperature gradients in the LED consistent with those of an operating, product-level LED, thereby ensuring accurate binning of the LED.

26 Claims, 17 Drawing Sheets

Related U.S. Application Data

(60) Provisional application No. 61/560,614, filed on Nov. 16, 2011, provisional application No. 61/559,411, filed on Nov. 14, 2011.

(51) Int. Cl.
| | | |
|---|---|---|
| *G01N 21/66* | (2006.01) | |
| *G01N 21/71* | (2006.01) | |
| *H01L 33/32* | (2010.01) | |
| *H01L 33/44* | (2010.01) | |

(56) References Cited

U.S. PATENT DOCUMENTS

| | | |
|---|---|---|
| 2006/0028155 A1 | 2/2006 | Young |
| 2006/0170923 A1 | 8/2006 | Schmitt |
| 2007/0241691 A1* | 10/2007 | Okumura .................. H01J 9/50 315/169.4 |
| 2007/0295956 A1* | 12/2007 | Haitko ............... C08G 59/3245 257/40 |
| 2008/0014726 A1* | 1/2008 | Cha ................... H01L 21/02381 438/487 |
| 2009/0154525 A1* | 6/2009 | Dai .......................... G01K 7/01 374/178 |
| 2009/0236506 A1 | 9/2009 | Dudgeon et al. |
| 2010/0127282 A1 | 5/2010 | Harbers et al. |
| 2010/0295442 A1 | 11/2010 | Harbers et al. |
| 2010/0327872 A1 | 12/2010 | Chen et al. |
| 2011/0025337 A1* | 2/2011 | Morrow ................. G01R 31/26 324/414 |
| 2012/0267647 A1* | 10/2012 | Kim .................... H01L 25/0753 257/88 |

FOREIGN PATENT DOCUMENTS

| | | |
|---|---|---|
| CN | 102193053 | 9/2011 |
| TW | 200925571 | 6/2009 |

OTHER PUBLICATIONS

Bahadur, M. et al. "Silicone Materials for LED Packaging", 6th International Conference on Solid State Lighting, Proc. of SPIE, vol. 6337, 63370F-1 (2006), 7 pgs.
Bechtel, H. et al. "Lumiramic—A New Phosphor Technology for High Performance Solid State Light Sources", 8th International Conference on Solid State Lighting, Proc. of SPIE, vol. 7058, 70580E-1 (2008), 10 pgs.
Bera, D. et al. "Enhancement of quality of downconverted white light", Journal of Photonics for Energy, Proc. of SPIE, 016501-1, vol. 1 (2011), 12 pgs.
Bolt, B. "LED test", Cascade Microtech, Test and Measurement World, Sep. 2010, pp. 37-43.
Bridgelux ES Array Series, Product Data Sheet DS17, Jul. 29, 2011, pp. 1-31.
Bridgelux, Micro SM4, Product Data Sheet DS27, Mar. 28, 2012, pp. 1-23.
Chen, K. et al. "Integration of Phosphor Printing and Encapsulant Dispensing Processes for Wafer Level LED Array Packaging", 11th International Conference on Electronic Packaging Technology and High Density Packaging, 2010 IEEE, pp. 1386-1392.
Chilla, J. et al. "Recent Advances in Optically Pumped Semiconductor Lasers", Proc. of SPIE 6451, 645109-1 (2007), 10 pgs.
Christensen, A. et al. "Thermal Management Methods for Compact High Power LED Arrays", 7th International Conference on Solid State Lighting, Proc. of SPIE, vol. 6669, 66690Z (2007).
DeGroot, A. et al. "Highly transparent silicone materials", Linear and Nonlinear Optics of Organic Materials IV, Proc. of SPIE, vol. 5517, 2004, pp. 116-123.
DeLoach, L. et al. "Transition Metal-Doped Zinc Chalcogenides: Spectroscopy and Laser Demonstration of a New Class of Gain Material", IEEE Journal of Quantum Electronics, vol. 32, No. 6, Jun. 1996, pp. 885-895.
Fan, B. et al. "Thermal Study of High-Power Nitride-Based Flip-Chip Light Emitting Diodes", IEEE Transactions on Electron Devices, vol. 55, No. 12, Dec. 2008, pp. 3375-3382.
Fitzpatrick, R. "Mie scattering", May 18, 2002, Online document available at http://farside.ph.utexas.edu/teaching/jk1/lectures/node103.html.
Fujita, S. et al. "Luminescence Characteristics of YAG Glass-Ceramic Phosphor for White LED", IEEE Journal of Selected Topics in Quantum Electronics, vol. 14, No. 5, Sep. 2008, pp. 1387-1391.
Gosnell, J. et al. "Light Scattering by White-Emitting CdSe Nanocrystals and Traditional YAG:Ce3+ Phosphor Particles", Mater. Res. Soc. Symp. Proc. vol. 1148, 1148-PP09-02 (2009), 6 pgs.
Gu, Y. et al. "A Non-contact Method for Determining Junction Temperature of Phosphor-Converted White LEDs", 3rd International Conference on Solid State Lighting, Proc. of SPIE, vol. 5187 (2004), pp. 107-114.
Guo, G. et al. "Methods to improve the fluorescence intensity of CaS:Eu2+ red-emitting phosphor for white LED", Materials Science and Engineering B 130 (2006), pp. 189-193.
Hansel, R. A. et al. "Temperature Dependant Fluorescence of Ce-doped Garnets for Use as Thermographic Phosphors", Jul. 20, 2008, 11 pgs.
Ho, W. et al. "Mid-infrared reflectance of silicone resin coating on metal substrates: Effect of polymeric binders' absorption", Infrared Physics and Technology, 38 (1997), pp. 123-131.
Hoelen, C. et al. "Remote phosphor LED modules for general illumination-towards 200 lm/W general lighting LED light sources", 8th International Conference on Solid State Lighting, Proc. of SPIE, vol. 7058, 70580M-1 (2008), 10 pgs.
Hsu, Y. et al. "Decay Mechanisms of Lumen and Chromaticity for High-Power Phosphor-Based White-Light-Emitting Diodes in Thermal Aging", 2008 Electronic Components and Technology Conference, 2008 IEEE, pp. 779-782.
Hu, Y. et al. "Preparation and luminescent properties of (Ca1—xSrx)S:Eu2+ red-emitting phosphor for white LED", Journal of Luminescence 111 (2005), pp. 139-145.
Ibanez, J. et al. "Far-infrared transmission in GaN, AlN, and AlGaN thin films grown by molecular beam epitaxy", Journal of Applied Physics, vol. 104, No. 3, Aug. 2008, 033544, 7 pgs.
Jayasinghe, L. et al. "Is the Thermal Resistant Coefficient of High Power LEDs Constant?" 7th International Conference on Solid State Lighting, Proc. of SPIE, vol. 6669, 666911 (2007), 7 pgs.
Lipp, E. D. "Near-Infrared Spectroscopy of Silicon-Containing Materials", Applied Spectroscopy Reviews, 27(4), (1992) pp. 385-408.
Philips Lumileds, Luxeon LED Application Brief AB32, 2012, 39 pages, www.philipslumileds.com/uploads/252/ab32-pdf.
Philips Lumileds, Luxeon Rebel ES Product Brief 61, 2012, 2 pages, www.philipslumileds.com/uploads/251/PB61-pdf.
Ma, M. et al. "EpiEL: Electroluminescence directly on LED epiwafers", 7th International Conference on Solid State Lighting, Proc. of SPIE, vol. 6669, 666910 (2007), 6 pgs.

(56) References Cited

OTHER PUBLICATIONS

Mirov, S. B. et al. "Erbium fiber laser-pumped continuous-wave microchip Cr+2:ZnS and Cr+2:ZnSe lasers", Optics Letters, Jun. 1, 2002, vol. 27, No. 11, pp. 909-911.

Muller, B. et al. "Development of a fast fiber-optic two-color pyrometer for the temperature measurement of surfaces with varying emissivities", Review of Scientific Instruments, vol. 72, No. 8, Aug. 2001, pp. 3366-3374.

Norris, A. et al. "Novel Silicone Materials for LED Packaging", 5th International Conference on Solid State Lighting, Proc. of SPIE, vol. 5941, 594115-1 (2005), 7 pgs.

Setlur, A. et al. "Phosphor quenching in LED packages: measurements, mechanisms, and paths forward," 9th International Conference on Solid State Lighting, Proc. of SPIE, vol. 7422, 74220E-1 (2009), 8 pgs.

Shen, C. et al. "White LED based on CaAl2Si2O8:Eu+2, Mn2+ phosphor and CdS/ZnS quantum dots", 3rd International Photonics and OptoElectronics Meetings (POEM 2010), Journal of Physics: Conference Series 276 (2011) 012184, pp. 1-4.

Sorokina, I. T. et al. "Novel mid-infrared random powder lasers Cr/sup 2+/:ZnS vs. Cr/sup 2+/:ZnSe", International Quantum Electronics Conference (IQEC), May 21, 2004, pp. 736-738.

Tran, N. T. et al. "Effect of Phosphor Particle Size on Luminous Efficacy of Phosphor-Converted White LED", Journal of Lightwave Technology, vol. 27, No. 22, Nov. 15, 2009, pp. 5145-5150.

Trevisanello, L. et al. "Accelerated Life Test of High Brightness Light Emitting Diodes", IEEE Transactions on Device and Materials Reliability, vol. 8, No. 2, Jun. 2008, pp. 304-311.

Vanlathem, E. et al. "Novel Silicone Materials for LED Packaging and Opto-electronics devices", Organic Optoelectronics and Photonics II, Proc. of SPIE, vol. 6192, 619202 (2006), 8 pgs.

Yamamoto, H. "White LED Phosphors: the next step", Optical Components and Materials VII, Proc. of SPIE, vol. 7598, 759808-1 (2010), 10 pgs.

Zhu, Y. et al. "Investigation of the Optical Properties of Yag:Ce Phosphor", 6th International Conference on Solid State Lighting, Proc. of SPIE 6337, 63370S (2006), 9 pgs.

* cited by examiner

HIGH THROUGHPUT HOT TESTING METHOD AND SYSTEM FOR HIGH-BRIGHTNESS LIGHT-EMITTING DIODES

RELATED APPLICATIONS

This application is a continuation of U.S. patent application Ser. No. 13/673,947 entitled "HIGH THROUGHPUT HOT TESTING METHOD AND SYSTEM FOR HIGH-BRIGHTNESS LIGHT-EMITTING DIODES" filed Nov. 9, 2012 which claims priority of U.S. Provisional Patent Application Ser. No. 61/559,411, entitled "HBLED High Throughput Hot testing Method And Instrument" filed Nov. 14, 2011 and U.S. Provisional Patent Application Ser. No. 61/560,614, entitled "HBLED High Throughput Hot testing Method And Instrument" filed Nov. 16, 2011.

BACKGROUND OF THE INVENTION

1. Field of the Invention

The present invention is related to a method for quickly establishing hot test conditions representative of those expected in operational solid state LED products including packaged high-brightness light-emitting diodes (HBLEDs) or phosphor-converted HBLEDs (pc-HBLEDs) (hereinafter both called HBLEDs). The present invention is also related to a system that can rapidly provide the hot test conditions as well as high-precision measurement of optical properties of the HBLEDs.

2. Related Art

FIG. 1 illustrates an exemplary HBLED 100 including a phosphor layer 102 and a thin, e.g. a few μ thick, indium-gallium-nitride (InGaN) film 101. In typical embodiments, phosphor layer 102 is also applied to the sides of InGaN film 101. Phosphor layer 102 includes the luminescent phosphors, i.e. the microcrystals containing active visible light emitting ions. Phosphor layer 102 further includes either a binder, such as silicone, or a sintered crystal (described in further detail below). The InGaN film/phosphor layer combination is mounted on a submount 104 and then encapsulated using a lens 103 of approximately 2 mm in radius. Lens 103 is formed using silicone, which increases light extraction by closely matching the refractive index of the surface of phosphor layer 102.

HBLED 100 may be inspected at the wafer-level, either un-singulated or singulated, at varying stages of processing. When HBLED 100 is assembled into a product-level HBLED, submount 104 can be further attached to a printed circuit board as well as to a heat sink.

Generally, the photometric parameters of HBLEDs are measured during electrical probe tests. Exemplary photometric parameters include the CCT (correlated color temperature, i.e. a metric that relates the appearance of emitted light to the appearance of a theoretical heated black body that combines red, orange, yellow, white, and blue light in varying degrees to form white light in various locations along the Planckian curve), chromaticity (the quality of a color regardless of its luminance, that is, as determined by its hue and colorfulness: saturation, chroma, intensity, or excitation purity), and CRI (color rendering index, i.e. the principal metric of the CIE (International Commission on Illumination) system that uses the averaged $R_i$ scores for eight standard test colors or similar color tests such as $R96_a$ and related tests). Probe tests are typically performed by applying a brief pulse of current to the InGaN film for a timescale typically between 10 msec and 200 msec while the optical properties of the HBLED are measured. Alternately, the electrical probe may be applied for a period of time exceeding that needed for the parametric measurement in order to attempt to bring the thermal condition of the HBLEDs to conditions more closely related to those expected in the final lighting product form.

Unfortunately, the use of electrical probes does not bring the HBLEDs to conditions anywhere near those expected in the final lighting product. The primary difficulty is due to the disparate thermal qualities of the materials used in the construction of the HBLEDs. These materials may include InGaN films, silicon or copper submounts, sapphire or SiC substrates, quartz materials for lenses or optical windows, and silicone encapsulants used to apply a slurry of microcrystalline paste, in which the microcrystals contain luminescing materials such as europium and cerium trivalent ions. Of particular note is an organic silicone phosphor carrier paste, which has a thermal conductivity at least two orders of magnitude and in most cases three orders of magnitude lower than the other enumerated materials, thereby resulting in a physical thermal time constant or response time of roughly three orders of magnitude longer than the other materials.

For example, InGaN film 101 has an operating temperature of roughly 60° C. above room temperature (85° C.), whereas phosphor layer 102, when including silicone, may reach an operating temperature of roughly 200° C. or more in some regions of some products. Note that the thermal time constant, i.e. the time to reach thermal equilibrium, for InGaN film 101 is roughly 10 msec, whereas for phosphor layer 102 can be from one to two seconds or longer. Not only are the thermal time constants different for the varying regions of HBLED 100 but, due to different dimensions and volumes, so are the heat capacities of the various regions. For both reasons, phosphor layer 102 is slower to heat than InGaN film 101.

Obtaining measurements for optical parameters with the materials at temperatures substantially different from anticipated operating temperatures of the final packaged product in a full luminiere yields incorrect results because the emitting wavelength and efficiency (intensity) of InGaN film 101 is moderately temperature dependent. More importantly, the absorption and emission spectra of the active phosphor ions in phosphor layer 102 as well as the quantum yield for the stokes-shifted emission radiation are also temperature dependent. It is therefore important that HBLED photometric properties (those related to the response of the human eye) be measured and reported at conditions as close to those anticipated in the final product as is possible.

Note that using electrical current from a probe to produce InGaN emission will bring InGaN film 101 to operating temperature within roughly 10 msec. The emitted blue radiation from the InGaN is absorbed by the active ions in the phosphors of phosphor layer 102, which in turn generates red or green or yellow (typically using (Eu+2) or (Ce+3) radiation from various host materials) as well as waste heat within microcrystals of the phosphor binder due to the Stokes shift of phosphor absorption and emission wavelengths and due to the temperature dependant non-radiational decay of each phosphor. However, the slow thermal response of the surrounding silicone in phosphor layer 102 requires that a full one to two seconds of excitation be maintained before the active phosphor ions can fully bring the surrounding silicone to the expected equilibrium operating temperature of nearly 200° C. in the surface adjacent to lens 103 (i.e. furthest from the InGaN film).

However, applying electrical excitation for one or two seconds to InGaN film 101 is not commercially attractive. Specifically, a high throughput tool needs to complete its measurement on the InGaN film within roughly 50 msec to process roughly seven 4-inch wafers (each containing roughly 10,000 die) per hour. Additionally, applying current for this duration heats InGaN film 101 well above its expected product operating temperature because the heat capacity of the film-submount is not sufficient to absorb the applied energy. To address this heating issue, HBLED 100 can be attached onto, for example, an extruded aluminum heat sink which adds heat capacity and convectively cools the overall structure in the product-level HBLED. However, this means that each HBLED 100 is singulated and then essentially packaged to near product form before it is tested. Thus, instead the film-submount at the wafer level is only attached to a film-frame carrier and therefore may only be exposed to current for 10-20 msec prior to exceeding its expected operating temperature. Thus, the application of heating energy to HBLED 100 through electrical current is insufficient to produce the expected operating conditions in the product-level HBLED. Thus, there is no accurate, commercially-viable hot testing of HBLEDs on the market today.

To address this shortcoming, the LED industry has used alternative tests. For example, in one test mode, the InGaN film is fabricated at the wafer level, then mounted onto a common roughly 1.6 mm thick alumina submount also at the wafer level. This alumina submount with widely spaced arrays thereon (mounted arrays) is next covered with a film of phosphors distributed in a silicone resin binder. Then, these mounted arrays are placed into an oven to a temperature of approximately 85° C. The mounted arrays are then powered electronically for roughly 10 milliseconds. Note that within these 10 msecs, the InGaN film and the phosphor region remain at approximately 85° C. At this point, the emission spectrum and average CIE coordinates for the entire alumina submount are recorded with all regions being nominally 85° C.

Unfortunately, with these temperature conditions for the measurement, color coordinate measurement accuracy is sacrificed. Specifically, it is well known that the temperature of the phosphor layer varies in the final product from roughly 85° C. near the InGaN film to temperatures as much as approximately 200° C. in the regions in contact with the thickest portion of the lens. The higher temperatures in the hottest regions of the phosphor layer give rise to increased non-radiative decay of the active ions and reduced conversion of blue pump radiation to longer wavelength phosphorescence, thus significantly shifting the final color coordinates of the HBLED (see FIG. 2). The exact amount of this shift is affected by the phosphor thickness, phosphor doping level, phosphor type, and additional factors. Many MacAdam ellipses of shift occur in changing the HBLED operating conditions from room temperature to 85° C. The shifts accelerate at higher temperatures.

As known by those skilled in the art, a MacAdam ellipse is an elliptical region centered on a target color on a chromaticity diagram. Each ellipse defines thresholds at which color difference becomes perceivable to the human eye. The sizes of the MacAdam ellipses are in steps, wherein any point on the boundary of a 1-step MacAdam ellipse represents one standard deviation of human perception of color mismatch between two test samples. Colors on the order of 2-step MacAdam ellipses of matching are generally considered desirable for high quality lighting applications. Color differences of a larger number of MacAdam ellipses are considered to be undesirable for high quality lighting in achromatic side-by-side lighting applications. Therefore, product bins of 5 MacAdam ellipses, and some insist as few as 3 ellipses, in size are not commercially attractive.

One relatively accurate technique for binning and color control includes using plates of phosphors, which are carefully hand-selected and combined with different luminescent emitters to achieve two-step MacAdam ellipse bins. Adjustable screws of phosphor converter can also be inserted into each device and tuned by moving their position at the top of the light producing chamber so that the bulb color coordinates are hand tuned. These hand-crafted LEDs are built one at a time in a fairly high-cost manufacturing process involving some trial and error. Currently, achieving product bins of 3-4 MacAdam ellipses in size, even using this intensive manufacturing technique, is difficult.

As shown above, current manufacturing processes are incapable of delivering fast, accurate, commercially-viable testing and binning for lighting applications. Therefore, an improved method is needed to produce operating conditions similar to those of the product-level HBLED, thereby allowing measurements relevant to customers.

SUMMARY OF THE INVENTION

A method of performing a hot test of a high-brightness light-emitting diode (HBLED) is described. The HBLED includes a InGaN film, a phosphor layer formed on the InGaN film, and a lens formed over the phosphor layer and the InGaN film. The method includes selectively heating portions of the phosphor layer using a laser to provide a predetermined temperature gradient in the phosphor layer. A current is applied to the InGaN film to provide a predetermined temperature within the InGaN film. Photometric measurements are performed on the HBLED after the selective heating and during the applied current once the InGaN film temperature is established.

The selective heating can directly heat the silicone in a silicone-based phosphor layer, or directly heat the active phosphor in a Lumiramic™-based phosphor layer (a phosphor composed of active ions contained within sintered ceramic host materials). Similarly, the laser can directly heat the active ion phosphors within silicone-bound phosphors. In one embodiment, the selective heating can be performed with a mid-infra-red (mid-IR) laser to directly heat the silicone binder. In another embodiment, the selective heating of the active ion phosphors can be performed with a visible tunable laser in either silicone- or Lumiramic-based phosphor layers. In yet another embodiment, the selective heating can be performed with an optically pumped semiconductor laser (OPSL) or an array of InGaN laser diodes to excite absorption bands either at 450 nm or in the region of nominally 465-485 nm. Tunable lasers such as dye lasers may be used for the 450 nm or 465-485 nm regions as well.

A system for hot testing of wafer-level packaged HBLEDs includes a laser, a probe tester, an integrating sphere, and a spectrometer system. The laser, which is positioned to direct its light onto an HBLED, is configured to selectively heat portions of the phosphor layer (e.g. heating the binder (IR) or the phosphor itself (visible)). In one embodiment, the laser is positioned to direct its light through the integrating sphere onto the HBLED. The probe tester is configured to apply current to the InGaN film of the HBLED to attain a predetermined temperature within the InGaN film and to, in turn, excite the phosphor during the color coordinate measurement. The integrating sphere is configured to collect light emitted by the HBLED during testing. The spectrometer system is configured to perform photometric measurements on light collected by the integrating sphere. The system may further include timing electronics coupled to the laser and the probe tester to synchronize operation of the laser and the probe tester. The system may yet further include a moveable wafer carrier for positioning the HBLED.

The integrating sphere may include an optical collar positioned directly above the HBLED configured to maximize the collection of light emitted from the HBLED at high angles (e.g. from 10 degrees to 170 degrees) into the integrating sphere during testing. This optical reflecting collar can be used to ensure that all HBLED light is collected during color coordinate measurement.

Another method of performing a hot test of a HBLED is described. The method includes using a first excitation source to establish a first predetermined operating condition of the phosphor binder, and a second excitation source to establish a second predetermined operating condition of the die. Photometric measurements on the HBLED can be performed after using the first and second excitation sources. Establishing the first predetermined operating condition can include providing a predetermined temperature gradient for the phosphor binder, and establishing the second predetermined operating condition can include providing a predetermined temperature for the InGaN film.

Using the first excitation source can include targeting the excitation of silicone or the active phosphor ions in the phosphor layer. For example, in one embodiment, using the first excitation source can include using an optical light source to selectively excite vibrational modes of silicone in the phosphor layer, thereby generating a temperature gradient in the phosphor binder. In another embodiment, using the first excitation source can include using an optical light source to selectively excite vibrational modes of methanol or a hydrocarbon wetting agent in the phosphor layer, thereby generating a temperature gradient in the phosphor layer. The second excitation source can include applying a current to the InGaN film.

In one embodiment, a wavelength of the first excitation source may be between 2.0 microns and 3.5 microns, and an average power of the coherent source may be between 100 watts and 12 watts for selectively exciting either one of silicone and methanol dopant wetting agents of the phosphor binder. In another embodiment, the wavelength of the first excitation source is between 0.45 microns and 0.53 microns, and an average power of the coherent source is between 100 watts and 12 watts. The system may further include a plurality of first excitation sources, which in combination provide an average coherent power of 12 watts or more.

The second excitation source may include an electrical probe tester. In one embodiment, the system may further include a plurality of second excitation sources.

The thermal diffusion time in a silicone-based phosphor layer and in a sintered ceramic-based phosphor layer have characteristic diffusion times of the order of msecs and 100 microseconds respectively for path lengths which are of the order of fractions of a phosphor thickness. Therefore, the temperature distribution established in the phosphor layer only maintains its initial profile or conditions for this period of time prior to being degraded by diffusion into both the InGaN film and lens proximate to the phosphor layer. Therefore, the color coordinate and brightness measurements are obtained within these characteristic times using a gated spectrometer for each phosphor layer type.

DETAILED DESCRIPTION OF THE DRAWINGS

In accordance with one aspect of an improved HBLED testing method, a laser is used to preheat the phosphor or binder prior to applying current to the InGaN film and then obtaining the photometric measurements of the wafer-level packaged HBLED. When silicone is used as a binder in the phosphor layer, the laser directly preheats the silicone, which in turn quickly brings the phosphor to the temperature distributions anticipated in the final product. In contrast, when a Lumiramic™ phosphor (a proprietary, sintered ceramic phosphor plate introduced by Philips Lumileds) is used as the phosphor layer, a laser directly heats the active ion in the phosphor, which in turn quickly brings the Lumiramic™ -based phosphor layer to the temperature distributions anticipated in the final product. Alternatively, in the case of silicone-based phosphor layers, laser excitation can be used to directly heat the active ion in the phosphor to establish the temperature distributions anticipated in the final product. In any of these embodiments, the subsequent photometric measurements are accurate representations of performance within the product-level HBLED. Photometric measurements include the CIE coordinates, CCT (correlated color temperature), chromaticity, and the CRI.

A number of factors contribute to CIE coordinate variation within a given product batch. These factors include phosphor particle size distribution, morphology, and particle shapes according to Mie scattering theories. Also contributing to CIE coordinate variation are non-uniformities in phosphor mixing concentrations, hot spots present on the InGaN film, as well as variations in forward voltage and efficiency (and therefore temperature) between the InGaN film and overall phosphor layer thickness (and therefore phosphor temperature distributions and electroluminescent conversion efficiency from blue to green and red wavelengths). The magnitudes of effect of some of these factors are described in detail below.

The performance of the InGaN film and its electroluminescence as well as the degree of non-radiative quenching of phosphorescence vary strongly with temperature, and directly affect the ratio of blue/red/green light in a LED. This performance directly affects the CIE coordinates. Thus, the precise operating temperature at each point in the phosphor must be obtained in order to correctly measure the product CIE coordinates and CCT.

Figure 2B:
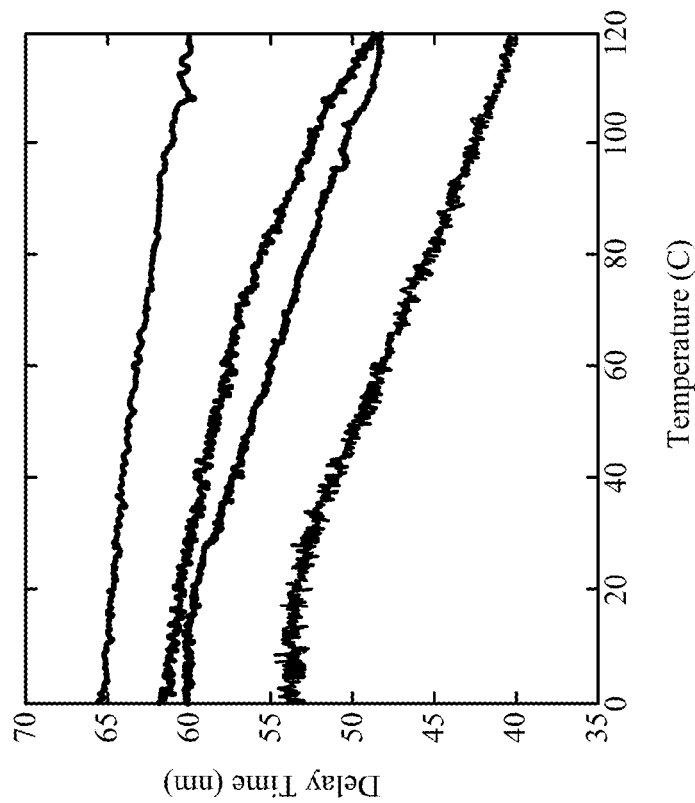
FIGS. 2A and 2B show graphs plotting decay time versus temperature of phosphors using two different emission filters.
Figure 2A:
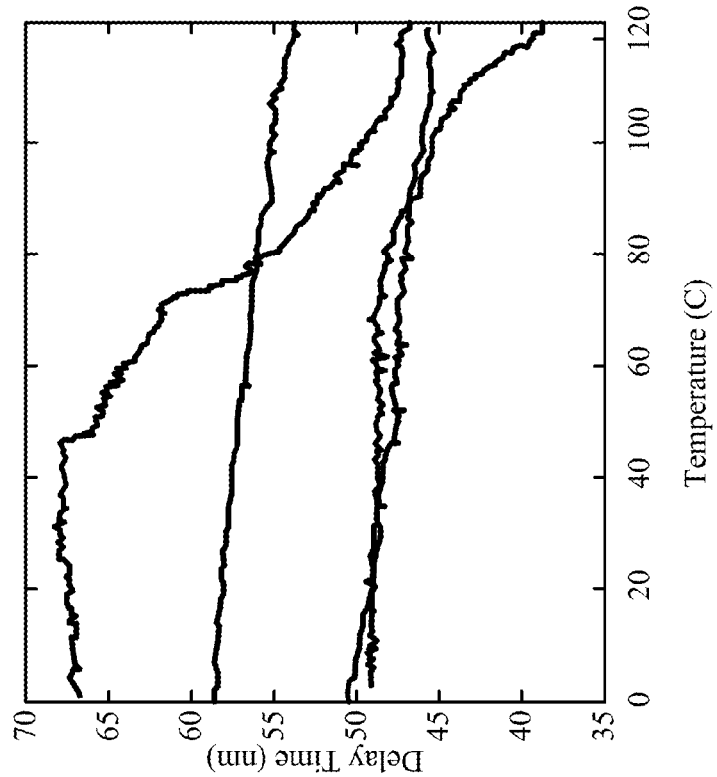

Those skilled in the art have quantified the variation in performance of samples of phosphor as a function of temperature, and have noted significant phosphorescent emission changes based on temperature variation. For example, FIGS. 2A and 2B illustrate the performance of four phosphors (specifically, $(YC_{1-x})_3(Al_{1-y}Ga_y)_5O_{12}$ phosphors) as a function of temperature using two different emission filters. FIG. 2A displays the change of 540 nm radiative decay time versus temperature and FIG. 2B displays the variation in 700 nm radiative decay versus temperature in these phosphors. To first order, the photon conversion efficiency from blue to either 540 nm or 700 nm radiation is proportional to the ratio of the decay time at elevated temperature to the decay time at lower (typically 25° C.) temperatures. As noted in FIGS. 2A and 2B, the phosphorescent emission (decay time) changed by up to a factor or two as temperature varied between 0° C. and 120° C. Some phosphors are even more temperature sensitive, wherein even greater temperature dependences are measured between room temperature and temperatures at 400° K and higher. Such temperature variations can produce substantial shifts in the CIE coordinates.

Figure 3:
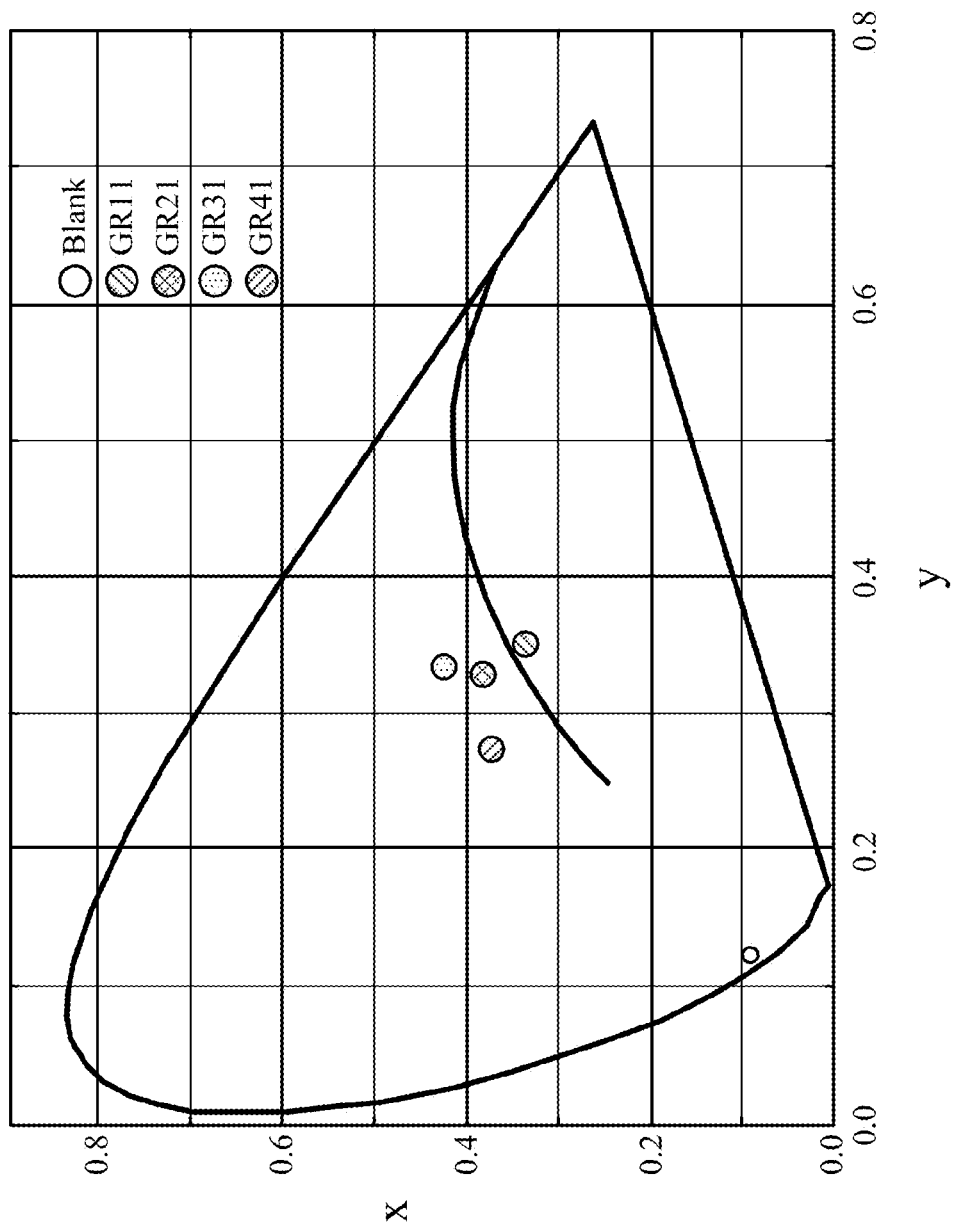
FIG. 3 illustrates the variation in CIE coordinates as a function of phosphor doping level for samples having different weight ratios of green to red phosphors.

Furthermore, changes within a given phosphor and phosphor mixtures within the same batch are affected by impurities, phosphor layer thickness, non-uniformity of phosphor doping, and irregular phosphor distributions. For example, FIG. 3 illustrates the variation in CIE coordinates as a function of phosphor doping level for different sample phosphors. Note that GR11 has equal parts green and red phosphors; GR21 has 2 parts green phosphors to one part red phosphor; GR31 has 3 parts green phosphors to one part red phosphor; and GR41 has 4 parts green phosphors to one part red phosphor. As shown by FIG. 3, varying the green to red phosphor weight ratio from 4 to 1 (80%) (GR41) to 3 to 1 (75%) (GR31) varied y− by as much as 0.08 and x− by as much as 0.025. CIE shifts within 0.005 or better in x− and/or in y− (which would be equivalent to an area of one MacAdam ellipse) would be optimal in the industry. However, as indicated by FIG. 3, variations in weight percentage of greater than 1.2% are sufficient to cause unacceptable CIE shifts.

Figure 4:
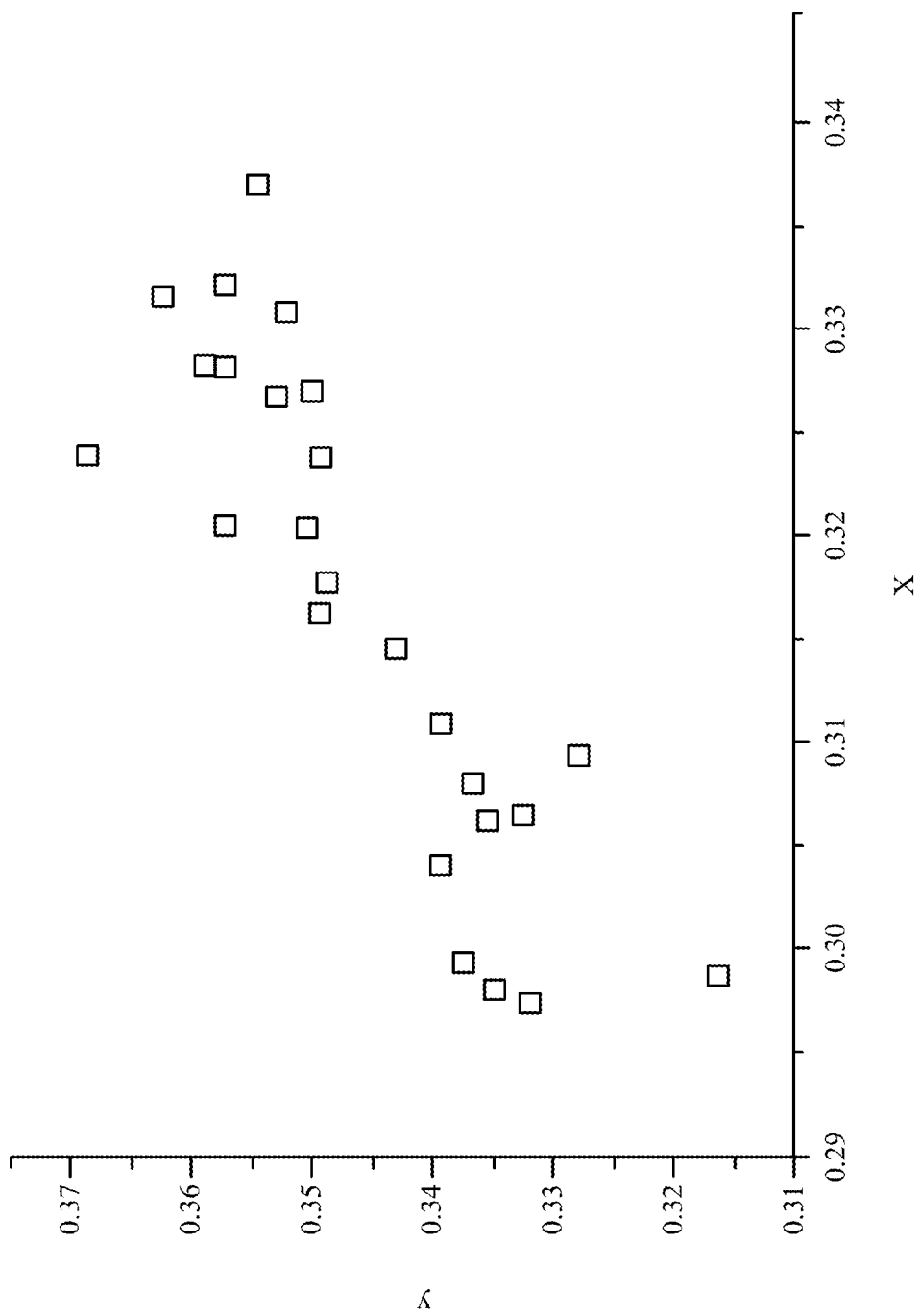
FIG. 4 shows the CIE variation for an exemplary phosphor binder in the case in which the phosphor was applied by a mechanical dispenser.

It is also known that CIE variations are also due to variations phosphor layer thickness and in "packing density", i.e. the fraction of the phosphor binder comprising phosphor as opposed to binder. For example, FIG. 4 shows the CIE variation for an exemplary dispensed phosphor layer.

Figure 5:
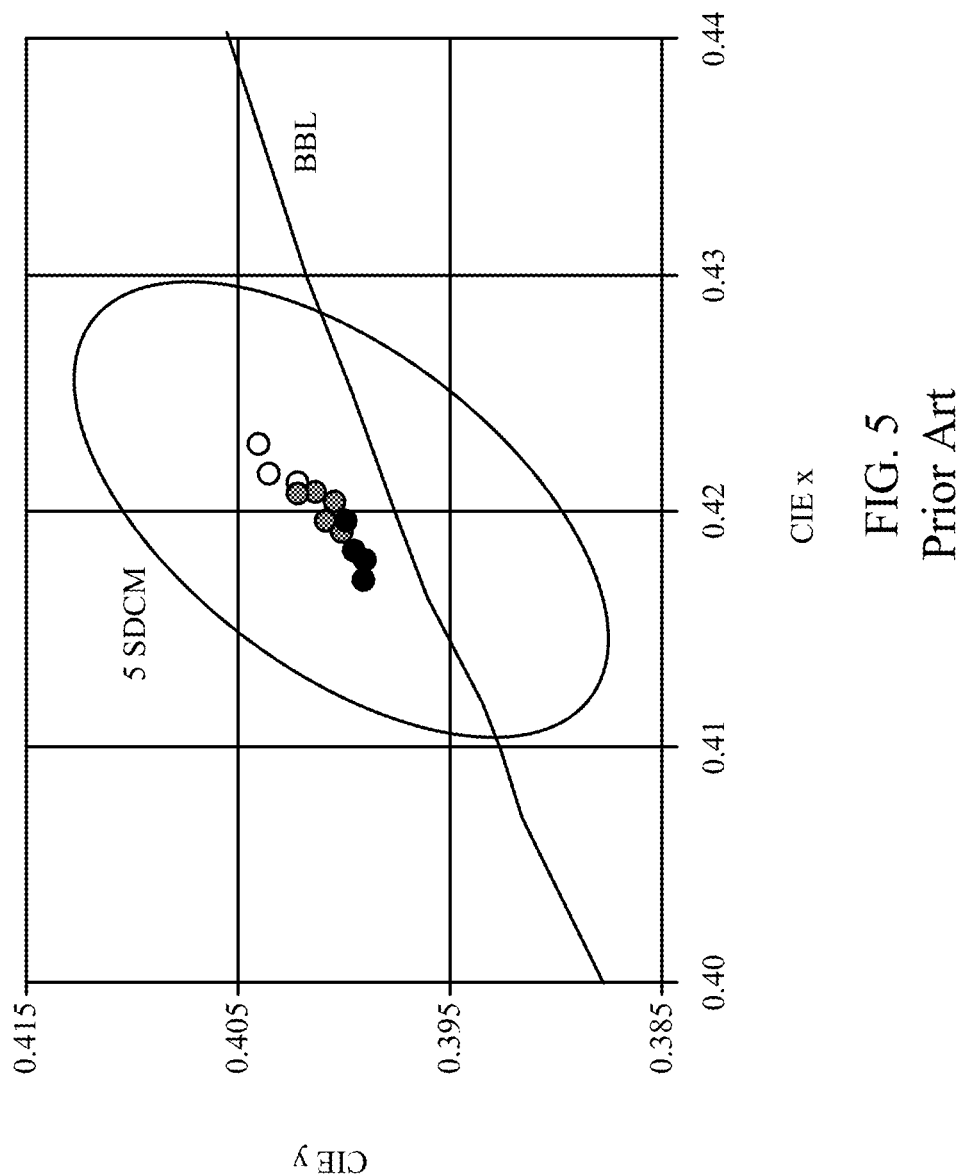
FIG. 5 shows a graph plotting CIE x– versus CIE y– for a phosphor mixture subjected to various currents and phosphor plate temperatures.

Changes in CIE coordinates of yellow, red, and orange phosphor have also been measured when either varying the drive current and/or the surface mount temperature. FIG. 5 shows a graph plotting CIE x− versus CIE y− for a phosphor mixture of red-orange-yellow subjected to currents from 800 mA to 100 mA (shown as black to white circles) with temperature variation from 25° C. to 85° C. The ellipse shown in FIG. 5 represents the 5 SDCM (standard deviation color match) from the color at the center of the ellipse, which in this case is 0.42 in x−. As shown in FIG. 5, the variation in CIE coordinates in changing the surface mount temperature (the phosphor also experiences heating from the Stokes shift of the absorbed light) corresponded to two MacAdam ellipses. Note that an additional one MacAdam ellipse variation from die to die at the same surface mount temperature may also occur. Thus, three ellipses of color point change, which is a significant change, may occur due to measuring at the wrong temperature and inconsistent fabrication uniformity.

In summary, there are many causes of CIE variation. Therefore, die-to-die hot testing is important in order to measure and identify within one MacAdam ellipse the CIE coordinates under final operating conditions within a product. Due to the multivariable nature of the die-phosphor performance, it is common knowledge within the industry that measuring at one temperature and extrapolating to another does not yield accurate results. Therefore, hot testing at the correct final product operating conditions must be performed.

Figure 1:
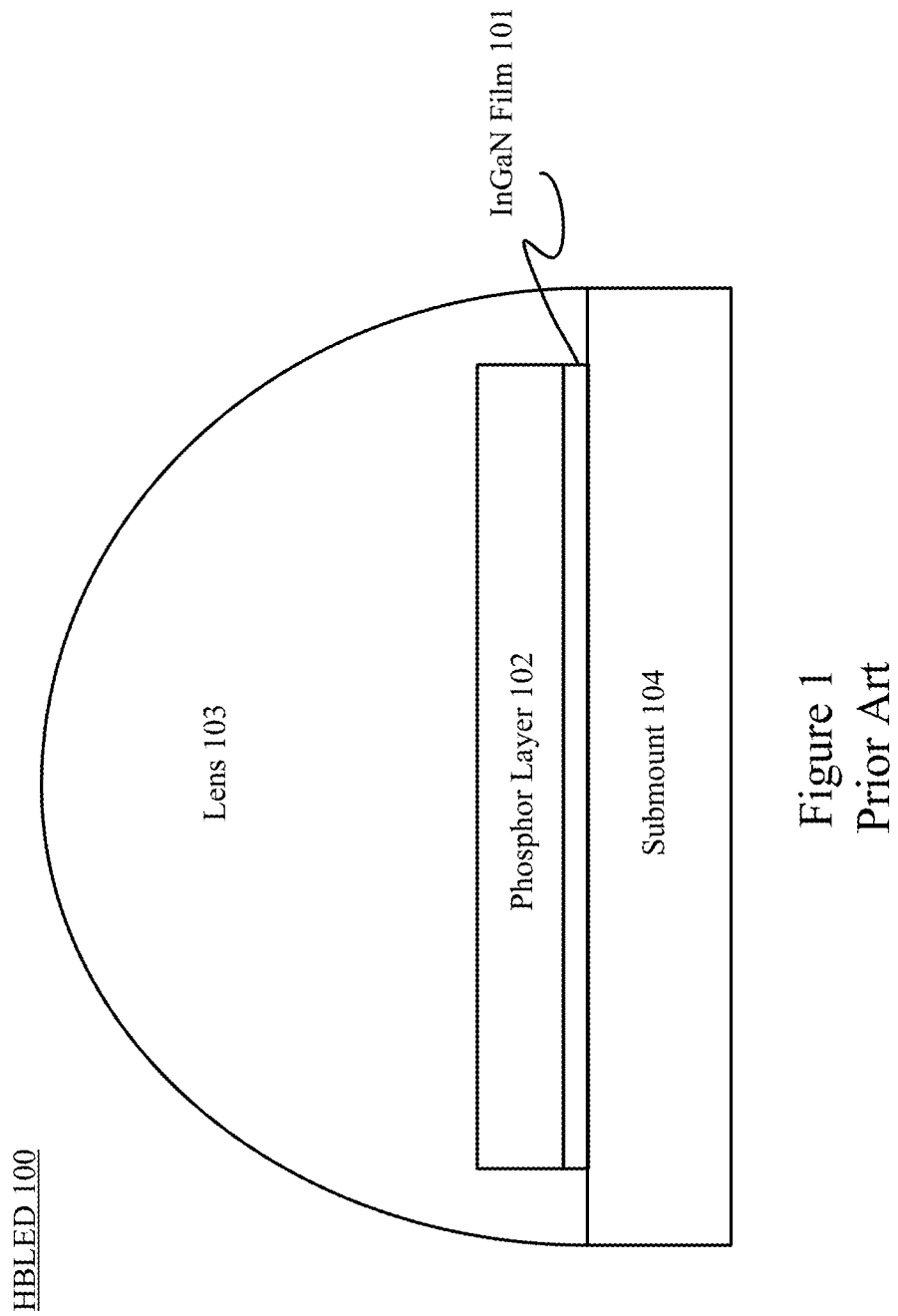
FIG. 1 illustrates an exemplary wafer-level packaged HBLED.

In accordance with one aspect of an improved HBLED hot test technique, after the wafer has been processed to include the InGaN film, the phosphor layer, the lenses, and submounts (see, e.g. FIG. 1) (generally referred to as "tiles" in the industry), the array of HBLEDs (or tiles) can be tested for photometric measurements. There are two principal factors giving rise to the difficulty of hot testing. A first factor, mentioned above, is the substantial differences in the properties of the materials used in the HBLED, particularly their thermal properties. For example, the p-n junctions are typically formed using the InGaN films, and the substrate materials are typically formed using sapphire or $Al_2O_3$, or silicon carbide, as examples. Generally, $Ce^{+3}$ (cerium) or $Eu^{+2}$ (europium) or related active ions are embedded in a range of micro-particle crystalline hosts, such as YAG (yttrium aluminum garnet), CaS (calcium sulfide), $Ca_{1-x}Sr_xS$ (calcium strontium sulfide), YAG-SiN (YAG-silicon nitride) and related crystalline host matrices, in the phosphor layer. A variety of silicone pastes can be used in forming the binder of a silicon-based phosphor layer. Additional materials used in the packaged HBLED include AlGaInP active films on GaAs or InP substrates for those manufacturers who use red LEDs rather than phosphors to generate the red portion of the white light spectrum. In flip chip applications, ceramic-based submounts are generally used as well. Often, quartz glass is used to provide a hermetic seal for the package as well. Lumileds has introduced Lumiramic™ phosphor layers in which high-temperature, sintered ceramics eliminate the need for silicone as a binder.

In one embodiment, the above materials are assembled onto submounts at the wafer level and tested prior to being singulated, cut, and trimmed for binning. Testing at the wafer level may include the measurement of the forward voltage resistance, luminous efficacy, CCT, and color spectrum (i.e. CIE coordinates) at the operating conditions of the die under conditions at which they will be used in the final LED product. Ideally, the color spectrum would be measured to within one MacAdam ellipse.

Figure 6:
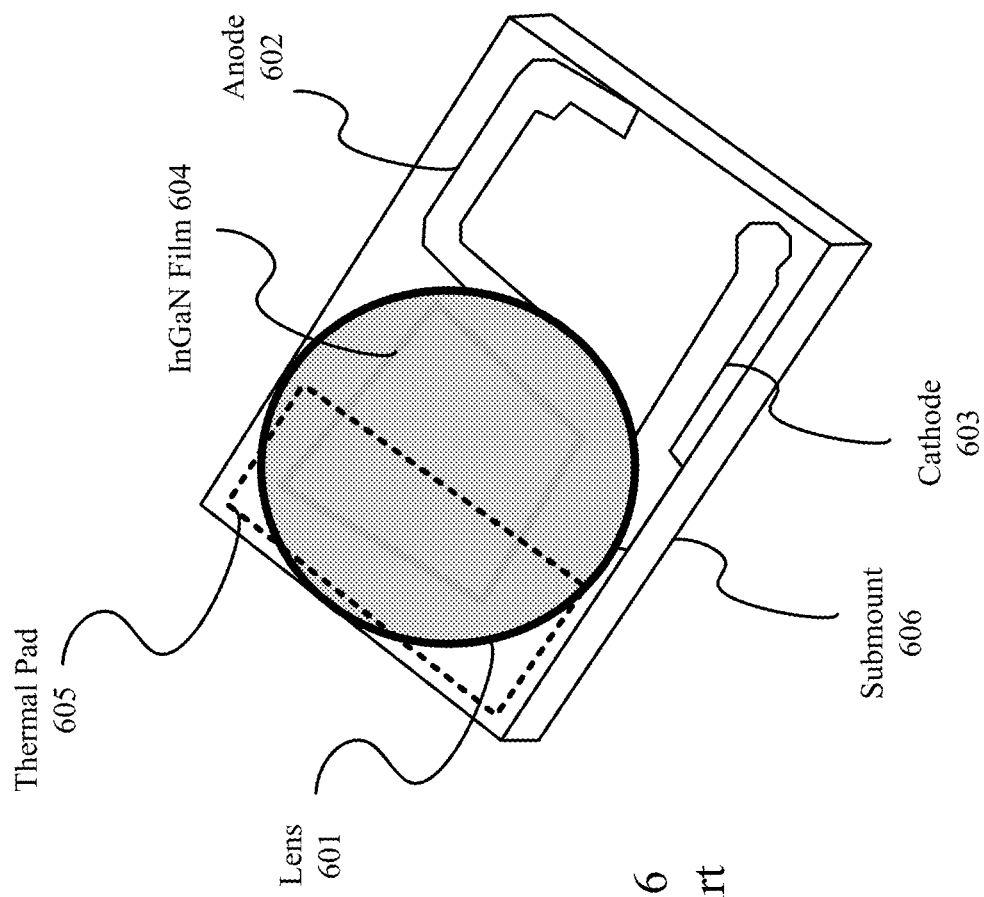
FIG. 6 illustrates an exemplary product-level HBLED.

A second factor in the difficulty of hot testing, related to the first, also mentioned above, is the difficulty in producing the operating conditions of the product-level HBLED while testing at the wafer-level, i.e. prior to incorporation into the final lighting product. As described above, in the product-level packaged HBLED plus phosphor, its various materials operate at substantially different temperatures. For example, an exemplary InGaN film driven with 900 mA of current may reach 85° C. or higher, which is well above room temperature. This is a consequence of the efficiency of the InGaN film itself, and the thermal resistivity from the InGaN film, through the submount, and onto the heat sink (e.g. the convectively-cooled extruded aluminum fins) on the product-level HBLED. On the other hand, the phosphor layer with silicone as a binder operates at much higher temperatures, e.g. around 200° C. on the surface facing away from the InGaN film. In the product-level HBLED, heat sinks allow for operation with these high temperatures. FIG. 6 illustrates an exemplary product-level HBLED, prior to attaching to a heat sink, including an InGaN film 604 encapsulated with a lens 601. A thermal pad 605, which is attached under a submount 606 and in electrical contact with InGaN film 604, provides an area for attaching to a heat sink. An anode 602 and a cathode 603, both of which are electrically connected to InGaN film 604 and form part of the wafer-level HBLED, are also shown.

The high temperature experienced by the top surface of the phosphor layer is because the silicone-based phosphor layer and the silicone of the lens, which is shaped to form the dome, has a thermal conductivity that is roughly one hundred to five hundred times less than every other material in the HBLED. Similarly, the thermalization time constant of the silicone lens is resultantly twenty-five times slower (thermal diffusion lengths are proportional to the square root of the material diffusion constant) and is in fact roughly one to two seconds while the other materials reach equilibrium operating conditions within roughly 10-20 msec. These significantly different operating temperatures and equilibration times pose significant challenges for hot testing of HBLEDs.

To measure a wafer-level packaged HBLED (i.e. prior to being attached to a heat sink) under the correct phosphor equilibrium temperature distributions, each InGaN film and adjacent phosphor needs to be heated for 1-2 seconds. Unfortunately, there is not sufficient thermal mass at this stage of the process to enable this heating as the InGaN blue emitting die film also reaches the elevated temperature of the phosphor. (This, in fact limits this approach to heating the entire tile to 85° C., the final product operating temperature of the InGaN film in the final SSL product, but this leaves the phosphor at temperatures much lower than those achieved in the final product.) Thus, the absence of an extruded aluminum heat sink (or similar heat sink) for each die, also poses significant challenges for hot testing of wafer-level, packaged HBLEDs.

To perform hot testing, an electrical current is applied to the InGaN film (for example, using anode 602 and cathode 603 of FIG. 6) during CIE coordinate measurement to provide the electroluminescence from the InGaN junction. (Note that photoluminescence is known to be an inadequate proxy for the film response as its conditions are significantly different from the electroluminescent response). Applying 900 milliamps of current to the InGaN film for 20 msec heats it to roughly 85° C., but the phosphor layer and the lens are not near their product-level operating conditions. Indeed, the only heat reaching the phosphor layer and the lens is due to (slow) thermal conduction from the InGaN film through the phosphor layer as well as the Stokes shift of the phosphor luminescence process. As a result, the phosphor layer reaches thermal equilibrium and provides its true color spectrum (i.e. the spectrum provided in the product-level HBLED) only after one to two seconds of optical excitation.

Note that simply applying electroluminescent excitation to the phosphor for two seconds is not an allowable solution for two reasons. First, for a four inch wafer with 10,000 LEDs, this excitation would take over 2 hours to test. LED manufacturers need an inspection speed from ten to even forty times faster than this to be cost effective. Second, and more importantly, providing current to the InGaN film for two seconds while unattached to a heat sink results in the InGaN film reaching an operating temperature so high that it quenches itself due to thermal rollover, thereby ensuring faulty CIE coordinate measurement.

Figure 7:
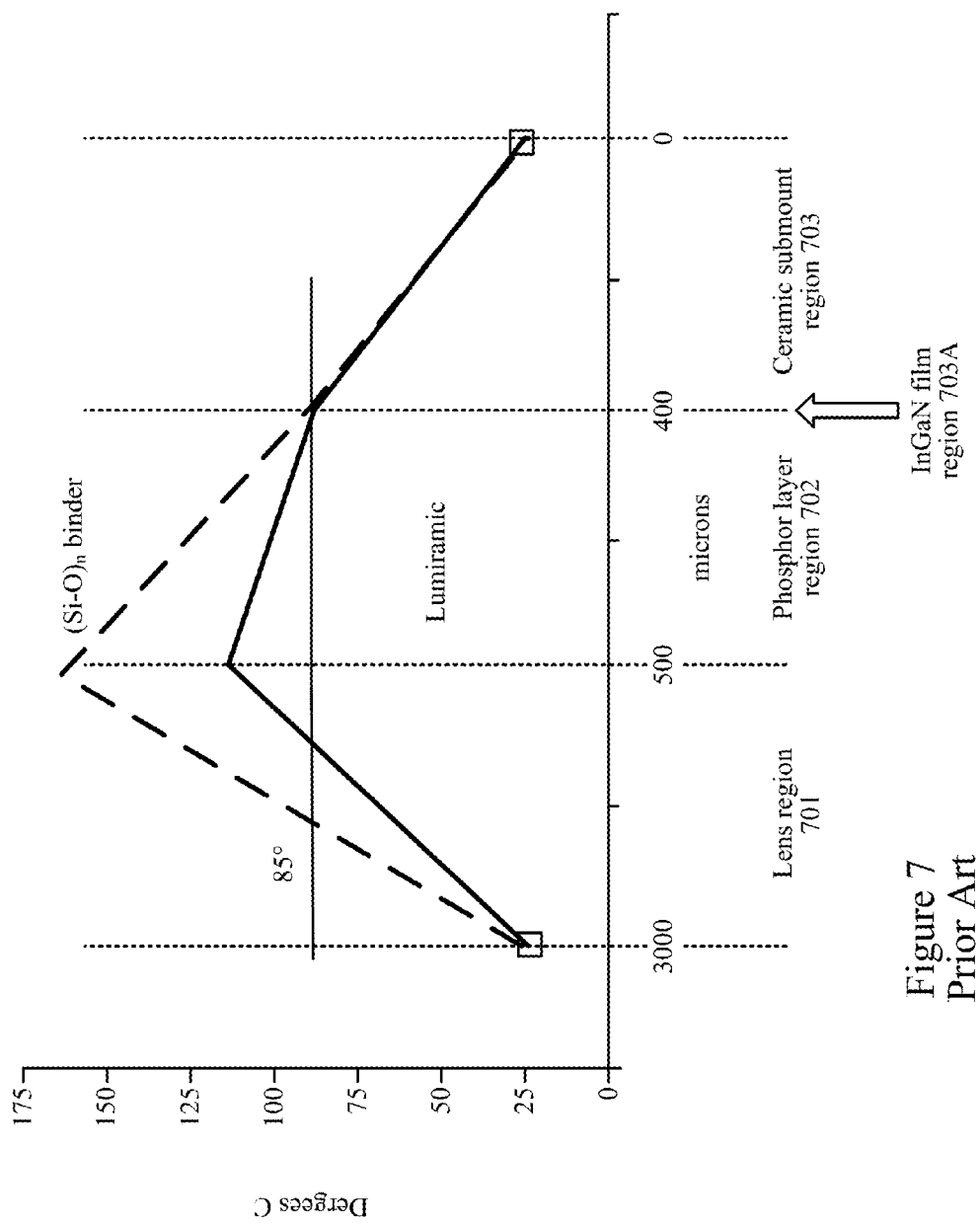
FIG. 7 illustrates exemplary temperature gradients in an exemplary wafer-level packaged HBLED.

Preheating the wafer-level packaged HBLEDs in an oven at 200° C. to achieve the proper peak temperature of the phosphor in the final product operational conditions is also not a viable solution as the correct thermal gradients within the phosphor layer are not produced. Specifically, the temperature within the phosphor layer is not one uniform temperature but to first order it is a linear gradient of from 200° C. or more at the surface furthest away from the InGaN film to 85° C. at the surface in contact with the InGaN film. The gradient is less severe for a phosphor layer formed with Lumiramic™, but still significant. For example, FIG. 7 illustrates exemplary temperature gradients from the bottom of a ceramic submount region 703, through a phosphor layer region 702 (the InGaN film region 703A provided for context), to the top of the lens region 701 of a product-level HBLED based on a silicone-based phosphor layer (dashed line) and a Lumiramic™-based phosphor layer (solid line). As noted in FIG. 7, at the interface to the lens region 701, the silicon-based phosphor layer may reach a temperature over 200° C., whereas the Lumiramic™-based phosphor layer may reach a temperature of over 100° C. This maximum temperature of the phosphor layer region 702 undergoes an essentially linear gradient to a reduced temperature of 85° C. at the interface to ceramic region 703.

Note that deviations from the linearities shown in the phosphor layer region 702 may exist due to the non-uniform doping within the phosphor layer. Specifically, phosphor crystal distribution within the phosphor layer is generally non-uniform. Regions of proximate phosphor crystals (which have diameters on the order of a few microns, but varying among manufacturers) will be hotter than phosphor microcrystals, which are substantially, uniformly situated within the phosphor layer. Therefore, the non-uniform distribution of phosphor crystals results in hot spots, which typically vary between LEDs. Note that the only real source of heat arising from within the phosphor layer is the active ions in the phosphor crystals. Thus, any hot spot testing should be able to reproduce hot spot temperatures as closely as possible.

The lens region 701 is used to protect the die from moisture as well as to aid in the extraction of light from the phosphor layer region 702. While lens region 701 does not contain any light emitting elements, it does act as an insulator. In contrast, the InGaN film 703A on ceramic submount region 703 acts as a heat conductor, which is opposite to the behavior of the lens region 701. Each of lens region 701 and phosphor layer region 702 exhibits a linear temperature gradient (although different temperature gradients, as shown in FIG. 7).

Note that preheating the wafer-level packaged HBLEDs to a somewhat higher temperature initially and then "topping off" the temperature by application of electroluminescence from the InGaN film holds the temperature for 1-2 seconds, which results in a hot test measurement of the InGaN film at 85° C., but the phosphor is still not at the correct elevated temperature and the phosphor layer does not exhibit the proper thermal gradient conditions. Thus, trying to achieve substantially different temperatures and temperature distributions within very different materials requires a more flexible approach.

As indicated above, it is important to attain the correct junction temperature as well as the correct phosphor layer temperature and temperature gradient for each wafer-level packaged HBLED. To that end, the hot testing should provide conditions that closely mimic actual operating temperatures and temperature gradients to provide consistently tight bins, which are desired to meet customer lighting applications.

Figure 8:
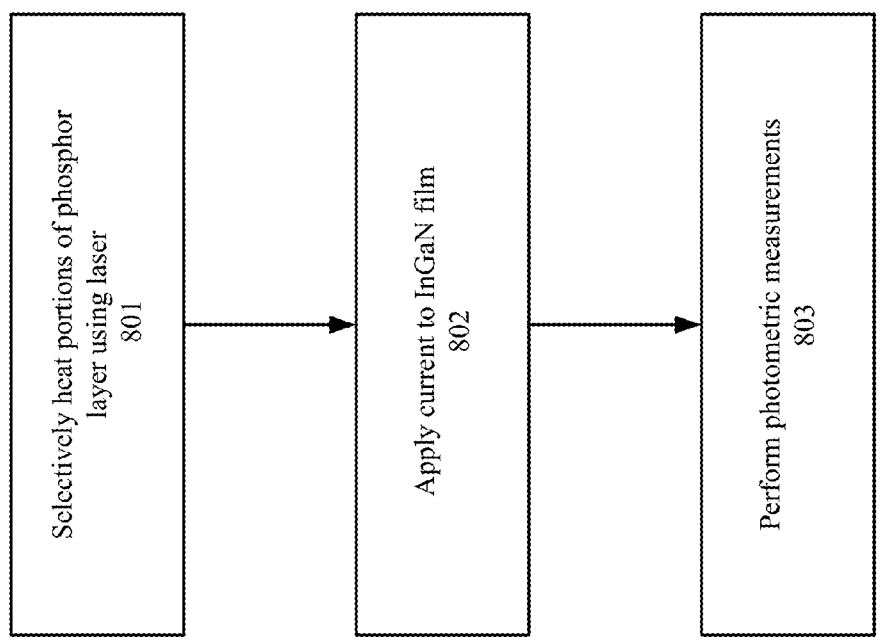
FIG. 8 illustrates an exemplary hot test technique for a wafer-level packaged HBLED.

FIG. 8 illustrates an exemplary hot test technique 800 that can provide accurate, high-throughput testing for wafer-level packaged HBLEDs. In step 801, portions of the phosphor layer can be selectively heated using a laser. Notably, by using selective laser heating, the correct temperature gradient in the phosphor layer can be quickly generated in a non-equilibrium manner, that is to say that the correct temperatures exist for a period of time prior to their degradation by diffusion to nearby layers of material in the HBLED package, without also heating the lens or nearby layers, such as the InGaN film. In one embodiment, this laser heating can include using mid-infrared (IR) radiation (e.g. wavelength of 850 nm to 900 nm) to heat the silicone binder of a silicone-based phosphor layer. Note that silicone is the only organic material in the package and therefore is the only material that absorbs optical radiation in the mid-IR region of the electromagnetic spectrum. All other materials used in the packaged HBLED are completely transparent in this region. Optical radiation in the region between 3.2 and 3.4 microns is absorbed by the combination vibrational modes of various types of silicones or other organics, which can be intentionally introduced as an additional material within the binder. In one embodiment, the wavelength of an IR tunable laser can be tuned to select an absorption depth of anywhere from a few microns to over 100 microns in the binder material.

In another embodiment, this laser heating can include using visible radiation to directly excite the active phosphor ions within the host crystals. Note that this embodiment can be used for any type of phosphor layer (e.g. the silicone-based phosphor layer or the Lumiramic™-based phosphor layer). In the case of the Lumiramic™-based phosphor layer, it is necessary to use a separate optical light source to directly excite the phosphors, thereby effectively serving as a proxy for the underlying InGaN film. An exemplary laser can include a frequency-doubled, optically-pumped semiconductor (OPS)) laser that operates with selected wavelengths between 390 nm to 750 nm. In one embodiment, a wavelength of 450 nm can be targeted. Other exemplary lasers include arrays of InGaN laser diodes or dye lasers.

In step 802, an appropriate current can be applied to the InGaN film, thereby quickly providing the correct temperature at the junction (i.e. for the InGaN film). Specifically, because the thermal response time of the InGaN film junction is on the order of 100 μsec, the film can reach the product-level operating temperature within this timescale as the waste heat generated by the current applied to the film within this time is sufficient to effect the correct temperature rise to 85° C. at the junction given the heat capacity of the film. With both the correct temperature gradient in the phosphor layer and the correct junction temperature now established, the photometric measurements can be made for the wafer-level packaged HBLED in step 803. Notably, these measurements can be made during the time constant in which they are preserved for a given phosphor material, whether silicone-based or Lumiramic™-based.

Notably, the selective heating using the laser advantageously decouples the heating time, heat capacities, and thermal time constants of the phosphor layer from the InGaN film and lens regions. As a result, the selective laser heating allows quick (high throughput), accurate, and well-defined temperature gradients to be created within the phosphor layer. These features of laser heating permit a manufacturer or other user to conveniently vary and map temperature distributions and final color coordinates against a range of customer operating conditions. As a result, an ordered HBLED can be confidently expected to perform based on the final package operating conditions.

The selective laser heating can also be done extremely fast. For example, a simple calculation of the heat capacity for a roughly 65 micron thick silicone layer shows that with only 10 mj of optical IR radiation the silicone matrix can be heated in less than 10 msec to its correct 180 degrees C. median or mid-range in z-operating point (or to any temperature anticipated by the manufacturer). Assuming that a laser has 12 watts of average power and operates at one kHz, as many as 1200 die can be processed per second (neglecting any optical losses in the testing tool). Therefore, when measuring four-inch wafers or tiles with 10,000 HBLEDs each, over 400 wafers or tiles per hour can be measured if all measurement operations are completed in 10 msec. In reality, the integration time of the spectrometer is likely in the range of 20 msec or more and there may be overhead time in the stage used to step from die to die.

Figure 9:
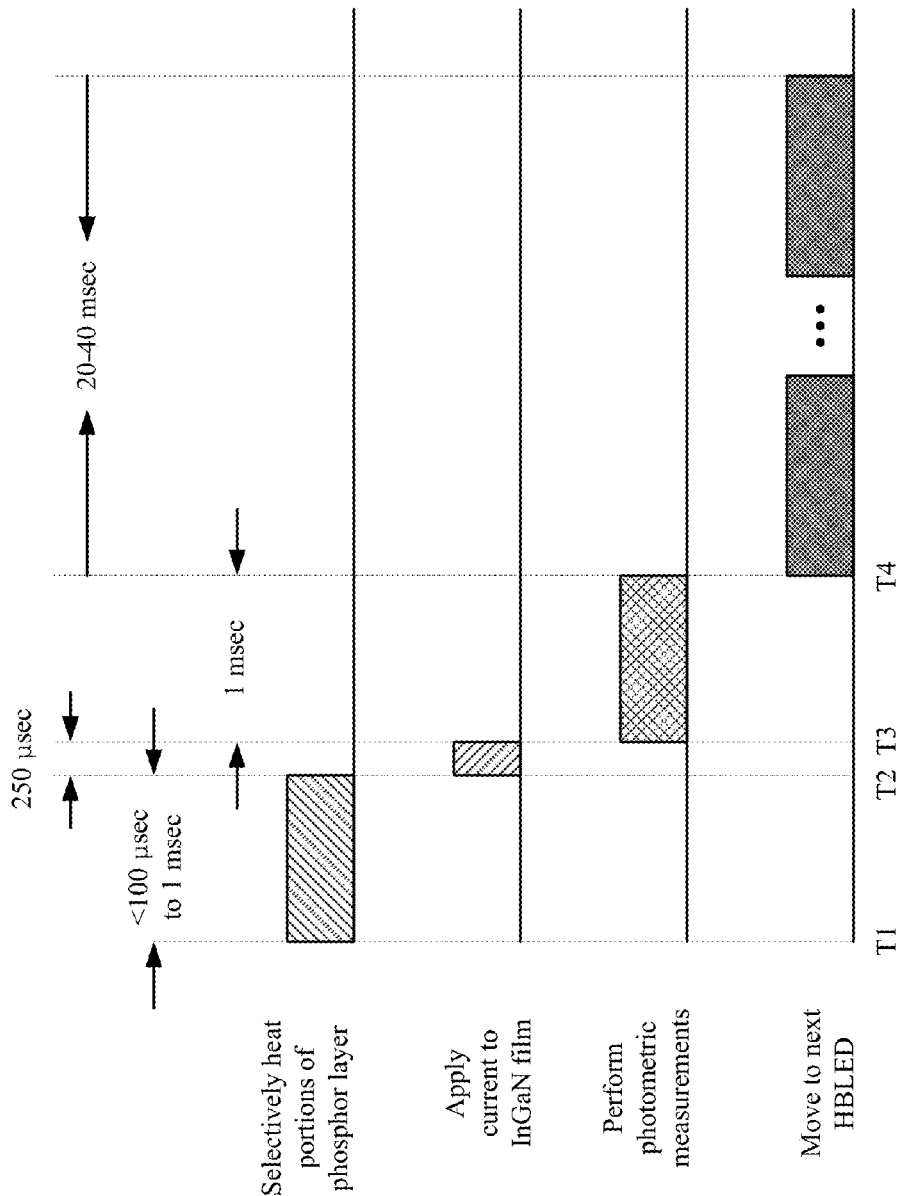
FIG. 9 illustrates exemplary timing sequences for a phosphor. Selective heating is applied for a period of between 1 μsec to 1 msec to avoid laser damage to the materials.

FIG. 9 illustrates exemplary timing sequences for a Lumiramic™-based phosphor layer and a silicone-based phosphor layer. At time T1, which indicated the start of a hot test for a wafer-level packaged HBLED, portions of the phosphor layer of that HBLED are selectively heated. The time period needed to perform this selective heating depends on whether the material to be heated is the silicone (in which case, the time period needed is approximately 1 msec) or the active ion in the phosphor itself (in which case, the time period needed is less than approximately 100 μsec). At time T2, approximately 250 μsec is provided to allow for the appropriate temperature gradients to propagate through the phosphor layer, and then current is applied to the InGaN film for a time period of approximately 50-100 μsec, which brings the InGaN film to 85° C. At time T3, the photometric measurements are taken for 1 msec or more. At time T4, the next wafer-level packaged HBLED is positioned for hot testing, which is conservatively estimated to take 20-40 msec. Taking the above times into account, a hot testing tool may be able to inspect and properly bin nearly 100 four-inch wafers or tiles per hour, which is 10× faster than any other currently marketed probe test tool. Advantageously, this reduced inspection and binning test time will significantly reduce the manufacturing cost for hot test operations.

Note that the temperature gradient provided by selective laser heating is non-equilibrium because it has not heated the boundaries of surrounding material to comparable temperatures. Therefore, CIE coordinate measurement is preferably made prior to the heat gradient distribution being modified by conduction of the deposited heat into the adjacent lens (above) and InGaN film (below) or before heat transport averages out the temperature distribution within the phosphor layer itself. A time-dependent model has been used to calculate the diffusion distance for heat transport within the phosphor layer for both silicone binders (diffusitivity of $1.3 \times 10^{-7}$ m$^2$/s) and Lumiramic™ phosphors (an assumed diffusivity of $4 \times 10^{-6}$ m$^2$/s as an upper limit). For phosphors of thickness approximately 200μ, the thermal profile degrades over a fraction (twenty percent) of this dimension in 2.5 ms for silicones and 0.1 ms for Lumiramic™ structures. Therefore, the CIE coordinates should preferably be made within this limited time after the profile is established. Note that this time scale applies whether the phosphor layer, silicone, (mid-IR) or the active phosphors (visible excitation) themselves are excited.

Figure 10:
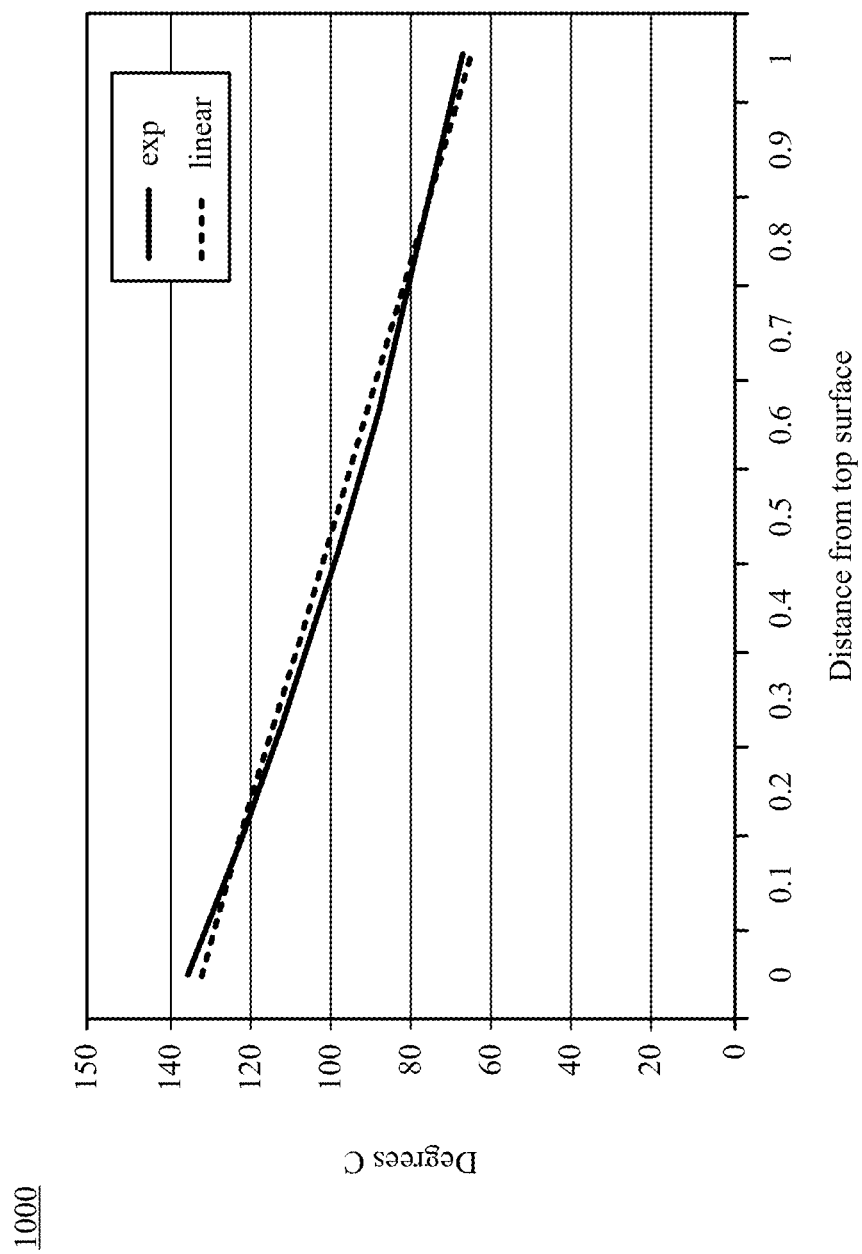
FIG. 10 illustrates a graph showing the phosphor region thermal profile obtained by tailoring absorption depth by tuning the laser to the correct absorption cross section.

In the embodiment that selectively laser heats the silicone of the phosphor layer, the temperature gradients are achieved by exciting the silicone at the proper wavelength in which the coupling of the near IR radiation is controlled to achieve nearly exactly the same distribution. FIG. 10 illustrates a graph 1000 that compares the linear gradient expected when the HBLED lamp is operated cw (continuous-wave) compared to the exponential attenuation and absorption of the mid-IR radiation. Notably, the two curves do not deviate from each other by more than 3° C. The overall median or average temperature can be achieved by controlling the number of millijoules in the exposure, and the correct temperature gradient can be achieved by operating the laser at the correct wavelength matched to the proper absorption cross section of the silicone material being used.

Figure 11:
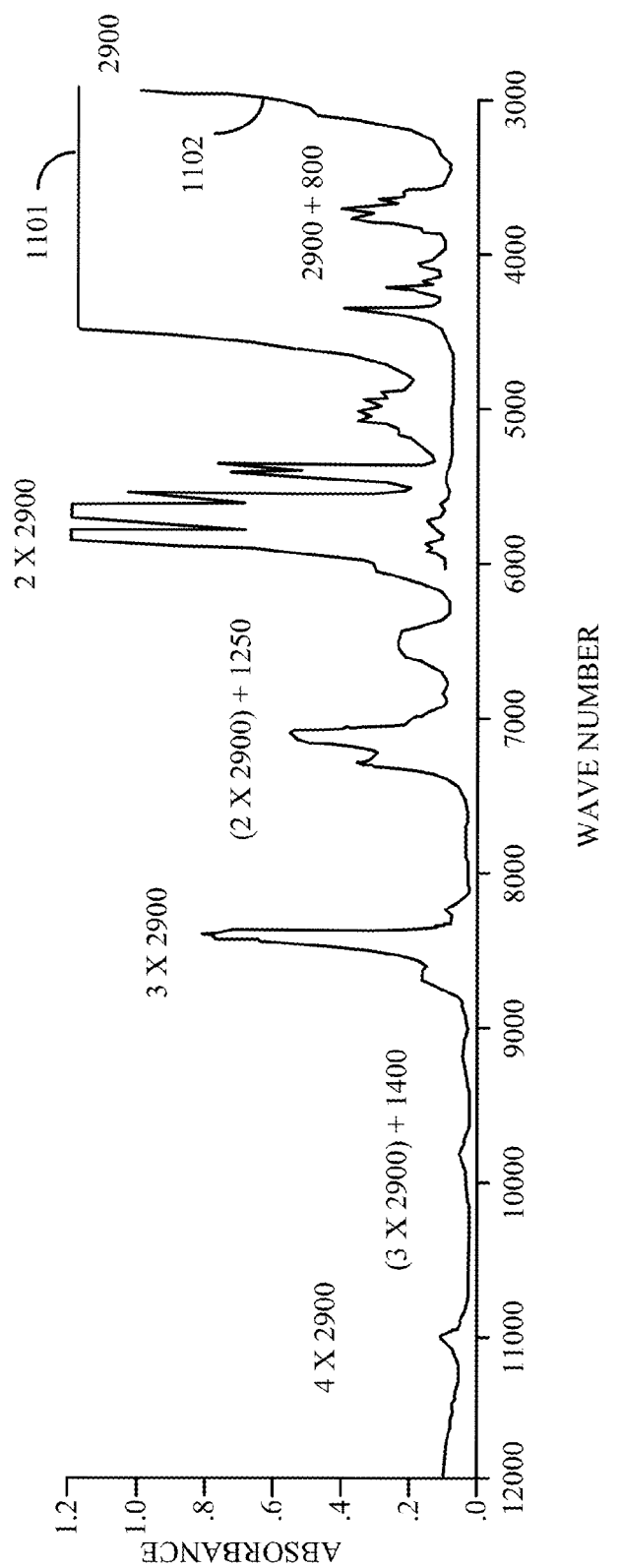
FIG. 11 illustrates the near-IR absorption and some mid-IR of PDMS.

Note that silicones in the phosphor layer may have cross links based upon vinyl groups, phenyl groups, methyl groups (e.g. PDMS (polydimethylsiloxane)), and related structures, each of which imparts a unique mid-IR absorption, index of refraction, CTE, and related mechanical properties to the binder. FIG. 11 illustrates the near-IR (12000-4000 cm$^{-1}$ (0.8-2.5 μm wavelength)) absorption and some mid-IR (4000-3000 cm$^{-1}$ (2.5-3.3 μm wavelength)) of PDMS with fundamental and certain combination bands labeled above their respective features. The spectrum of PDMS at thickness of 1 cm is labeled line 1101, and the spectrum of PDMS at thickness of 0.2 mm is labeled line 1102. The highest energy vibrational mode is the C—H (carbon-hydrogen) bond present at 3.3 microns. This strong absorption feature will also have accompanying combination bands near the maximum of the laser gain curve at 2.5 microns due to the combination with the R—Si bending mode at 11.7 microns and the stronger mode at 13 microns. The extinction coefficients for these and other silicone vibrational absorption bands may be extracted. The result is that the IR features of silicones have absorption depths near tens of microns for the C—H stretch and closer to a few microns for longer wavelength fundamental bands.

Figure 12A:
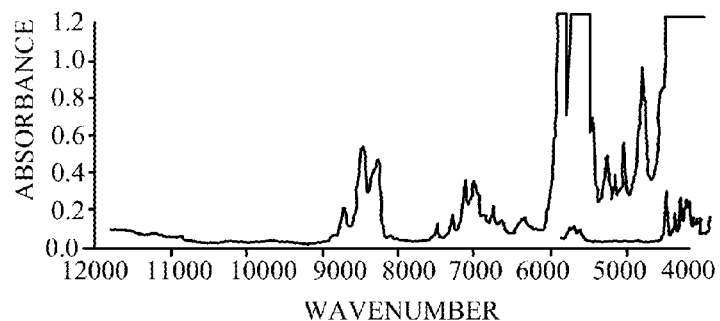
FIGS. 12A, 12B, and 12C show the near-IR and some mid-IR spectra for three different types of silicones.
Figure 12B:
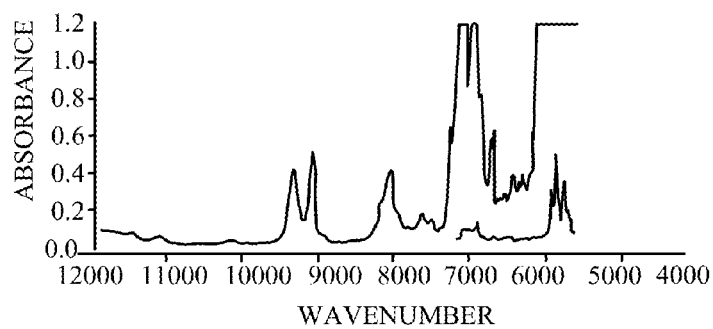
Figure 12C:
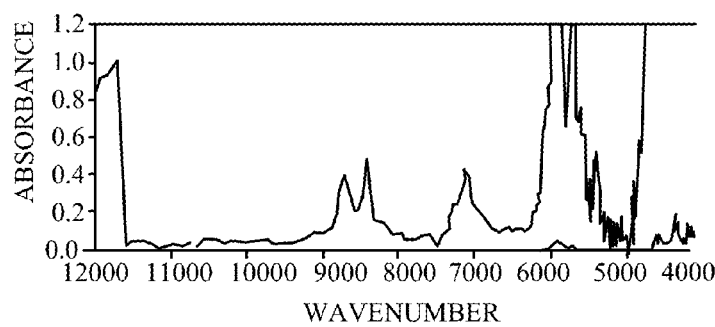

The various vibrational bands of different silicones may be shifted in energies by roughly as much as a few hundred cm$^{-1}$ from each other. FIGS. 12A and 12B show the near-IR and some mid-IR spectra for two silicone types, i.e. methyl-vinyl and phenyl, respectively. FIG. 12C show the near-IR and some mid-IR spectra for an exemplary lens sample made from a phenyl-based silicone which, along with vinyl based silicones, is blue shifted from PDMS. This shifting means that selectively exciting the underlying phosphor in the Lumiramic™-based phosphor layer requires that a wavelength longer than the fundamental vibrational wavelength will be needed to selectively excite the underlying phosphor without heating the overdome lens above it. Also note that the combination bands of FIGS. 12A and 12B have an absorption strength which is too small by a factor of roughly two for 100μ thick structures for providing the desired temperature gradients shown in FIG. 7.

In one embodiment, the phosphor layer can be doped with roughly one percent methanol, which may provide for the possibility of selective excitation in the mid-IR of the silicone even with a thick phenyl-silicone lens. Methanol will not affect the properties of silicones (other than its wetting onto substrates) and has the important feature that the O—H (oxygen-hydrogen) stretch lies at 3682 cm$^{-1}$ in the vapor phase and 3400 cm in the liquid phase, which is a full 500 cm$^{-1}$ away from the fundamental C—H stretches of all silicones. Using a 2% wetting solution when applying the phosphor layer may result in the ability to strongly and selectively excite the underlayer with an absorption depth on the order of 50-100 microns (or even thinner layers at higher concentrations). There is evidence that methanol does not affect the opacity, index of refraction, chemistry, thermal properties, or mechanical properties of the host silicones. Moreover, methanol may within hours diffuse from the sample and not affect LED performance.

Figure 13A:
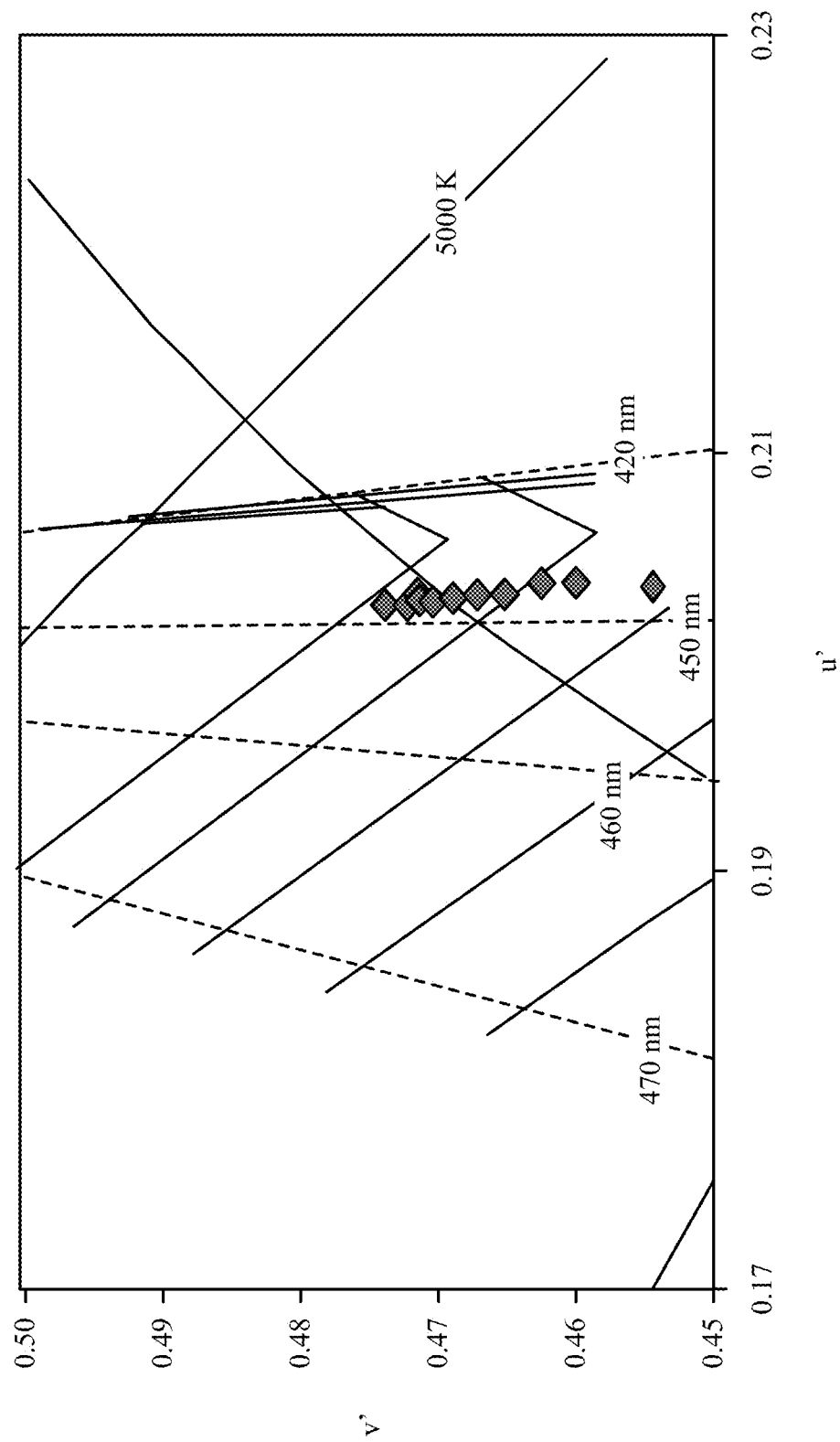
FIG. 13A shows exemplary U'V' CIE 1976 coordinates obtainable with differing blue emitting LEDs and differing Lumiramic™ plate thicknesses.
Figure 13B:
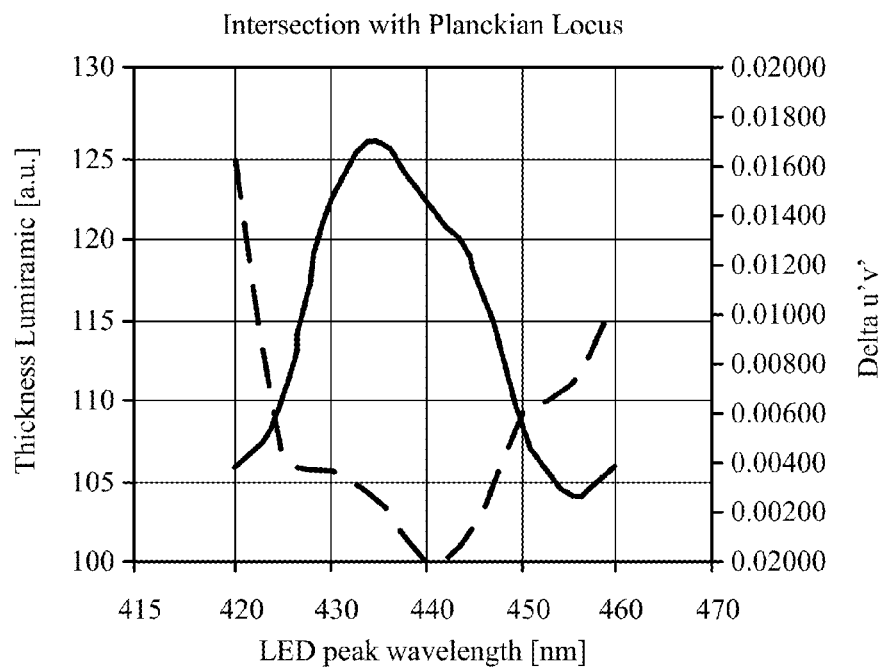
FIGS. 13B and 13C show the sensitivity Lumiramic™ plate thickness to varying blue emitting LEDs and resulting Du'v' deviation from Planckian locus and CCT using Ce:YAG phosphors.
Figure 13C:
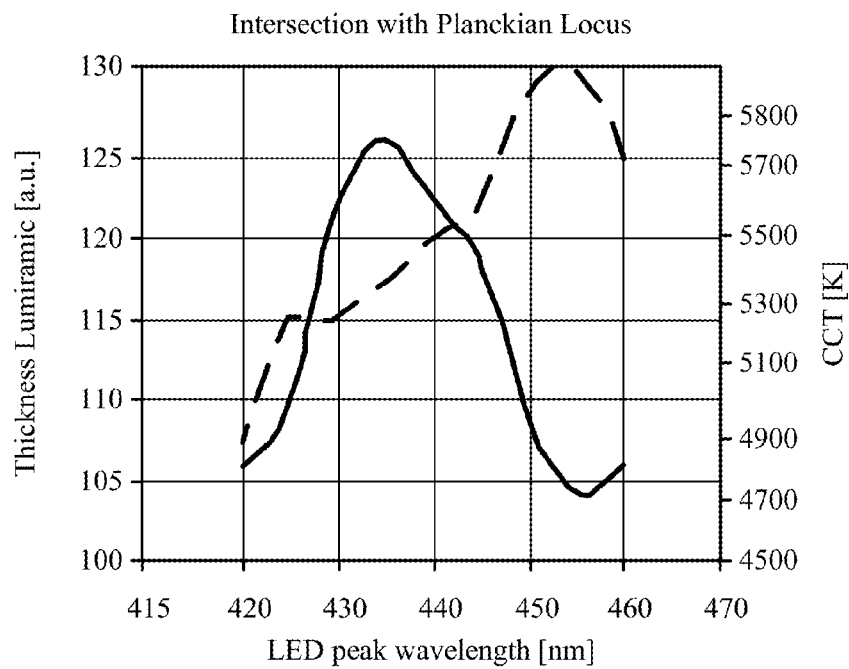

As noted above, in one embodiment, the direct excitation of the active ions of the phosphor can be used for non-silicone-based layers, such as those using sintered ceramics (e.g. Lumiramic™-based phosphor layers) as well as for silicone-based phosphor layers. Notably, the sintered ceramics are transparent in the mid-IR, just as are the remaining materials in these HBLEDs. FIGS. 13A, 13B, and 13C show variations in Lumiramic™ plate thickness and their effect upon Du'v' and CCT. Specifically, FIG. 13A shows the u'v' CIE 1976 coordinates obtainable with differing blue emitting LEDs (shown by dashed lines) and differing Lumiramic™ plate thicknesses (shown by solid diamonds). FIGS. 13B and 13C show the sensitivity of Lumiramic™ plate thickness to varying blue emitting LEDs (shown as solid lines) and resulting Du'v' deviation from Planckian locus (shown as dashed line in FIG. 13B) and CCT (shown as dashed line in FIG. 13C) using Ce:YAG phosphors. These variations and sensitivities support that HBLEDs should be hot tested in order to precisely bin CIE color coordinates within one MacAdam ellipse.

Directly exciting the phosphor active ions heats the phosphor and Lumiramic™ crystalline host material of the phosphor. An exemplary heat source to accomplish this excitation may include an OPSL (optically pumped semiconductor laser), which is wavelength settable (e.g. wavelengths from 350 nm to 600 nm). In one embodiment, a 460 nm wavelength settable OPSL centered near the strong absorption features of $Eu^{-2}$, $Ce^{+3}$, and related phosphors can be used as shown in FIG. 14. Thus, OPSLs can mimic the excitation of the blue InGaN LEDs. However, in preferred embodiments, OPSLs are used only to prepare the temperature gradient of the phosphor active ions and are not used providing the desired junction temperature of the InGaN die.

Figure 14A:
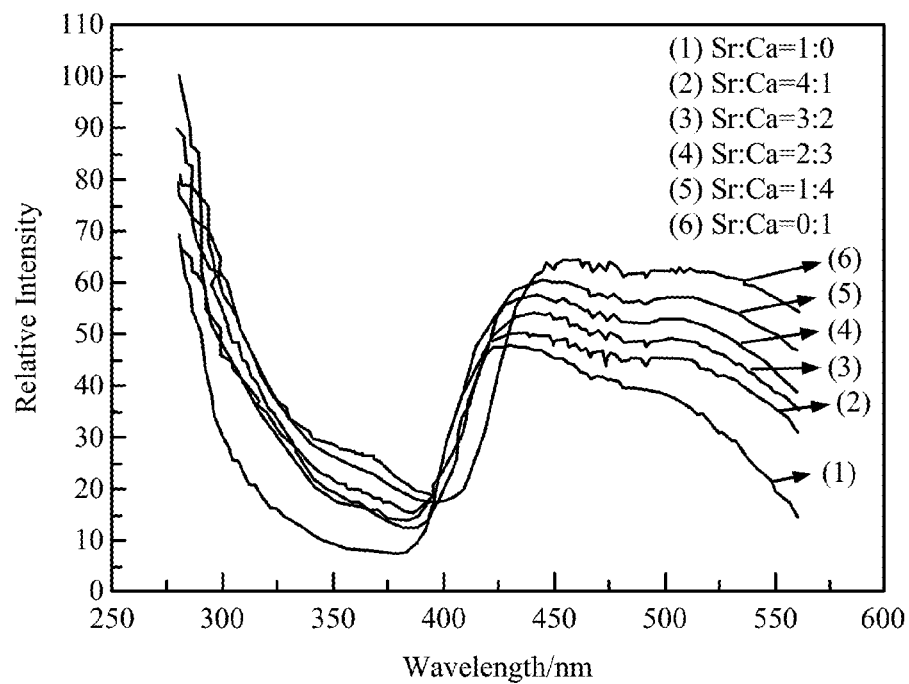
FIG. 14A and 14B show the excitation spectra of several example phosphors in various crystalline host types.
Figure 14B:
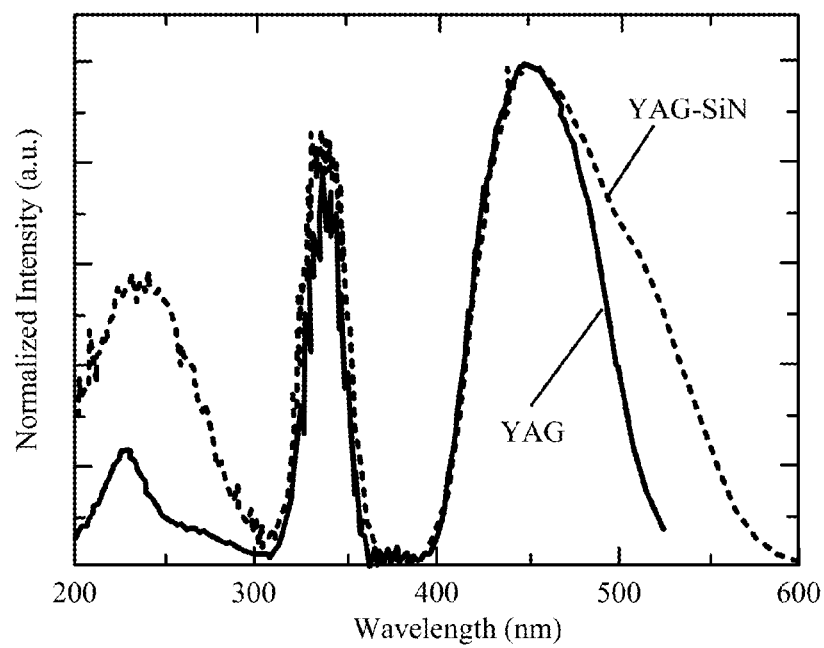

FIGS. 14A and 14B show the excitation spectra of two example phosphors in several crystalline host types. Specifically, FIG. 14A shows the excitation spectra of $(Ca_{1-x}Sr_x)$S:Eu+2 with different Sr:Ca ratios, whereas FIG. 14B shows the room temperature excitation spectra for $Ce^{3+}$ ion within its coordination sphere in $(Y_{0.97}Ce_{0.03})Al_{4.9}Si_{0.1}O_{11.9}N_{0.1}$ ($\lambda_{cm}$=720 nm; denoted as YAG-SiN) compared to the excitation spectrum for $(Y_{0.97}Ce_{0.03})_3Al_5O_{12}$ ($\lambda_{cm}$=560 nm; denoted as YAG).

Note that within the wavelength setability (as opposed to tunability) of an OPSL (between 460 and 530 nm), the absorption cross-section of the phosphors varies by over an order of magnitude. Because the excitation dose provides the average temperature, and the excitation coupling or absorption cross section determines the temperature gradient, the phosphor excitation can advantageously provide significant flexibility to precisely set the phosphor temperature gradients in z–, which are critical to achieving the proper hot test conditions and CIE coordinates.

In summary, HBLEDs having silicone-based phosphor layers or Lumiramic™-based phosphor layers can be hot tested using various phosphor heating strategies. The tradeoff between IR spectrum excitation of silicone binders versus visible spectrum excitation of active ion phosphors is that of absorption cross section flexibility (and therefore achievable temperature gradients) for the tunable mid-IR excitation approach versus using the more universal visible spectrum for direct excitation of phosphor active ions, which may provide flexibility to cover all phosphor package types.

As described above, the use of precision laser non-equilibrium heating followed by electroluminescent application using current and rapid photometric measurement extraction provides a flexible, accurate, and high throughput hot testing approach for the HBLED industry.

Note that an additional factor affecting the lateral (i.e. parallel to the plane of the quantum well) light distribution of both blue InGaN emission and phosphor emission can be strongly modified by Mie scattering within the phosphor region. Because the wavelength of the InGaN pump radiation can often approximate the dimensions of the phosphor microcrystals this means that the case of direct phosphor pumping may have its lateral heat deposition profile modified in the lateral dimension by Mie scattering. Mie scattering also exists for mid-IR excitation in the silicone binder pumping approach, but it is less severe.

Mie scattering describes the scattering of electromagnetic radiation by a sphere or other particle shape when the size of the particle is comparable to the wavelength of light traversing the medium. The well-known approximation of Rayleigh is that the intensity of scattered radiation I is given by:

$$I = I_0 \left[ \frac{1 + \cos^2\theta}{2R^2} \right] \left[ \frac{2\pi}{\lambda} \right] \left[ \frac{n^2 - 1}{n^2 + 1} \right] \left[ \frac{d}{2} \right]^6$$

where $I_0$ is the intensity of a beam of unpolarized light of wavelength $\lambda$, n is the refractive index of the particle, d is the diameter of the particle, and R is the distance to the particle.

Thus, the scattering of light should be considered when using wavelengths of light different for exciting the phosphor than will be encountered in the product-level HBLED phosphor excitation (i.e. wavelengths substantively different from those of the InGaN electroluminescence). This scattering is similar in extent in the case of hot testing with direct visible excitation of phosphors because the wavelength of the heat providing the hot test source and the electroluminescent source are very similar. However, attention should be paid to silicone-based phosphor hot testing where a mid-IR, rather than a blue wavelength of light, is used.

Figure 15:
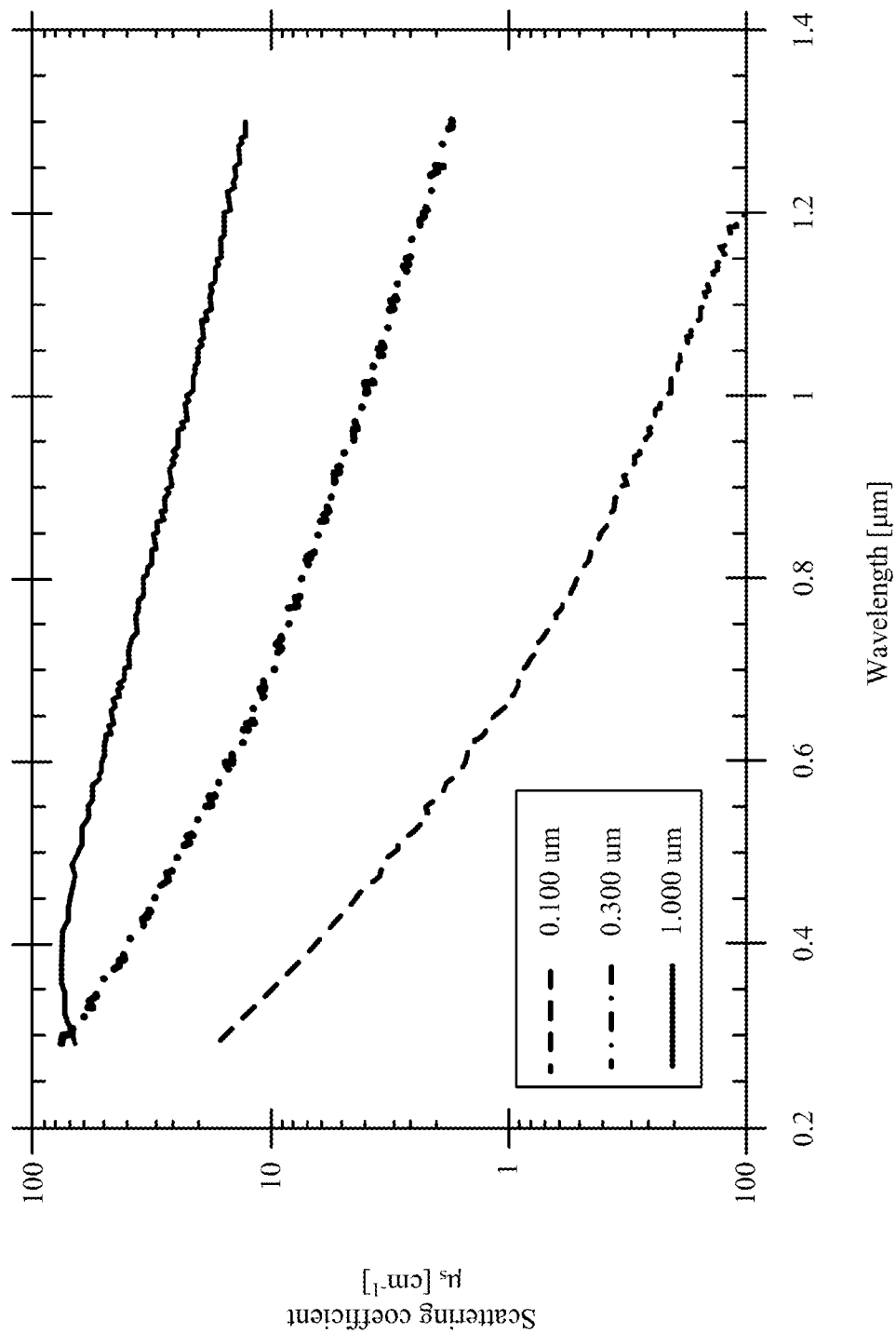
FIG. 15 illustrates the variation of Mie scattering coefficient versus wavelength for particles of various sizes.

FIG. 15 illustrates the variation of Mie scattering coefficient versus wavelength for particles of various sizes. Mie scattering for hot testing may provide a lateral temperature gradient different from that which will be obtained from cw electroluminescent illumination conditions. FIG. 15 indicates that the Mie scattering coefficient approaches that of the absorption depth in the phosphor only when the mean phosphor particle size is one micron or larger and it never exceeds the absorption length of order 100 microns for particles up to one micron. Therefore, the overall effects from MIE scattering on CIE measurements should be manageable.

Figure 16:
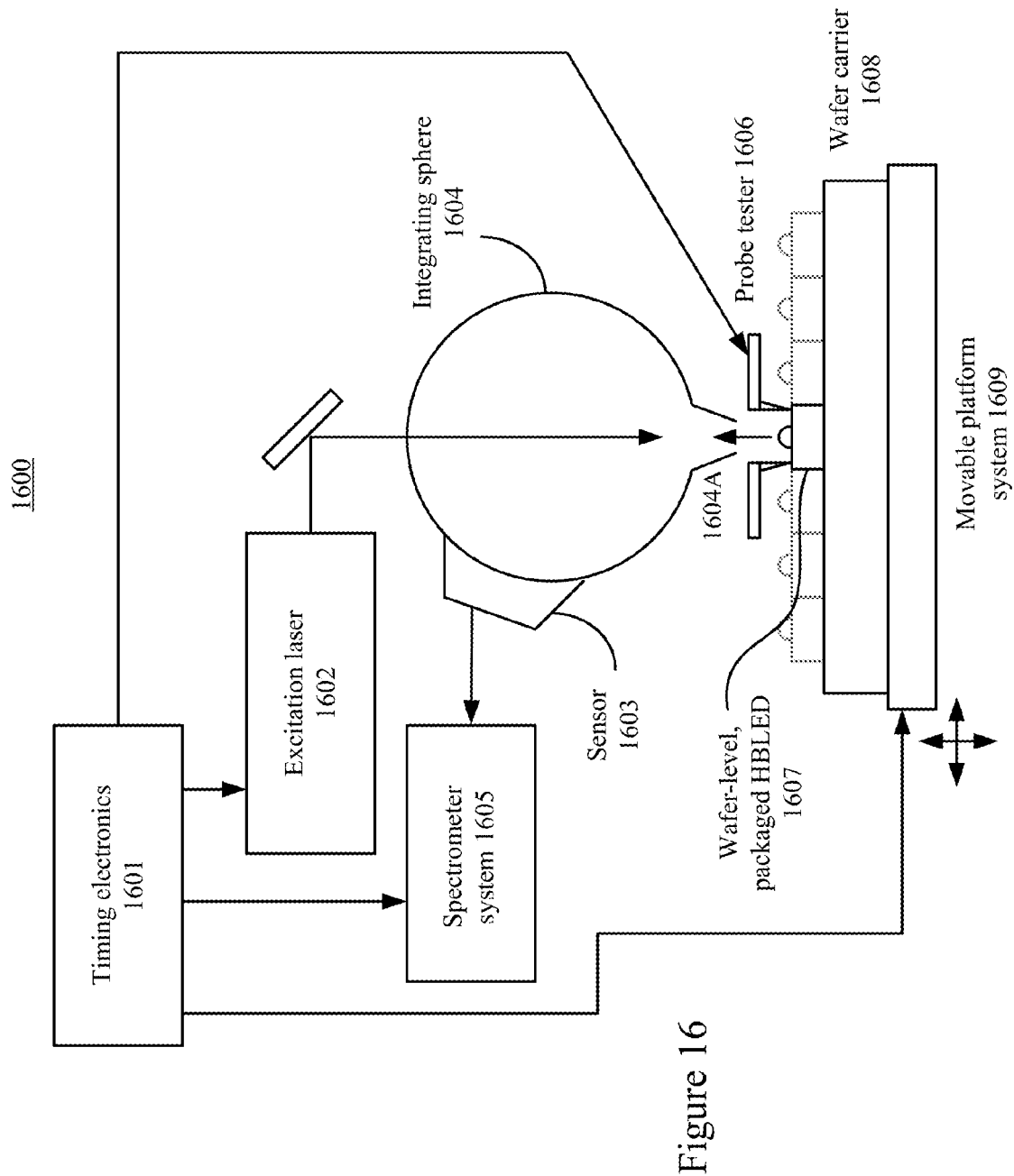
FIG. 16 illustrates an exemplary hot test system for testing of wafer-level packaged HBLEDs.

FIG. 16 illustrates an exemplary hot test system 1600 for testing of wafer-level packaged HBLEDs. An excitation laser 1602 is provided to excite portions of the phosphor or phosphor layer and establish the appropriate temperature gradient therein. A probe tester 1606 provides current to HBLED 1607 to bring the InGaN film to 85° C. In one embodiment, excitation laser 1602 and probe tester 1606 are controlled by timing electronics 1601 to provide the appropriate time periods of laser excitation and current application.

An integrating sphere 1604 (also known in the industry as Ulbricht spheres), having an interior surface that scatters light evenly over all angles, facilitates the collection of light from HBLED 1607 after laser excitation and current application. Integrating sphere 1604 is essentially an optical element consisting of a hollow spherical cavity with small holes for entrance and exit ports. In one embodiment of integrating sphere 1604, the entrance port can include a collar 1604A angled to provide a close fit around the lens of HBLED 1607 during hot testing, thereby ensuring that extraneous light to HBLED 1607 is not collected. Collar 1604A can include a high angle reflection optic that allows integrating sphere 1604 to collect light from HBLED 1607 at angles from 10° to 170°. In one embodiment (shown in FIG. 16), the light beam from excitation laser 1602 can be directed through integrating sphere 1604 to HBLED 1607. In other embodiments, the light beam can be directed obliquely onto HBLED 1607 without passing through integrating sphere 1604.

A sensor 1603, which is located at the exit port of integrating sphere 1604, can collect substantially all the light incident on the entrance port and provide the sum of that incident light to a spectrometer system 1605. Spectrometer systems 1605 can include a spectrometer and other well-known components, such as a computer, for performing photometric measurements of the light from HBLED 1607. In one embodiment, timing electronics 1601 can control spectrometer system 1605, thereby allowing timing synchronization with excitation laser 1602 and probe tester 1606. In one embodiment, sensor 1603 is gated off during the application of the laser when generating the phosphor non-equilibrium temperature distribution, and is only gated on during the application of the electroluminescent excitation radiation from HBLED 1607.

In one embodiment, a wafer carrier 1608 can hold HBLED 1607 and other HBLEDs in position during hot testing. Wafer carrier 1608, in some embodiments, can be coupled to a conventional movable platform system 1609, thereby allowing the hot testing of each HBLED on wafer carrier 1608. In one embodiment, timing electronics 1601 can also control platform system 1609 in the x-, y-, and z-planes.

Although illustrative embodiments of the invention have been described in detail herein with reference to the accompanying figures, it is to be understood that the invention is not limited to those precise embodiment. They are not intended to be exhaustive or to limit the invention to the precise forms disclosed. As such, many modifications and variations will be apparent to practitioners skilled in this art. For example, although HBLEDs are described herein, phosphor-converted HBLEDs (pc-HBLEDs) can be tested in substantially the same way using substantially the same systems. Moreover, although optically pumped semiconductors are described herein, other lasers such as dye lasers or InGaN lasers can also be used in application described above for optically pumped semiconductors. Accordingly, it is intended that the scope of the invention be defined by the following claims and their equivalents.

The invention claimed is:

1. A method of performing a hot test of a light-emitting diode (LED), the LED including an indium-gallium-nitride (InGaN) film, and a phosphor layer formed on the InGaN film, the method comprising:
   selectively heating portions of the phosphor layer using a laser to provide a predetermined temperature gradient in the phosphor layer;
   applying an electric current to the InGaN film to establish a predetermined temperature in the InGaN film; and
   performing photometric measurements on the LED while the phosphor layer is heated to the predetermined temperature gradient and while the InGaN film is heated to the predetermined temperature.

2. The method of claim 1, wherein the selectively heating directly heats silicone in the phosphor layer.

3. The method of claim 1, wherein the selectively heating is performed with a mid-infra-red (mid-IR) laser.

4. The method of claim 1, wherein the selectively heating is performed with a coherent laser.

5. The method of claim 1, wherein the selectively heating directly heats active phosphor ions.

6. The method of claim 1, wherein the selectively heating is performed with an InGaN laser to excite absorption bands near 460 nm.

7. A system for hot testing of light-emitting diodes (LEDs), each LED including an indium-gallium-nitride (InGaN) film, and a phosphor layer formed on the InGaN film, the system comprising:
   a laser positioned to direct its light onto an LED, the laser configured to selectively heat portions of the phosphor layer;
   a probe tester configured to apply an electric current to the InGaN film of the LED to establish a predetermined temperature in the InGaN film and to provide electroluminescence;
   an integrating sphere configured to collect light emitted by the LED during testing; and
   a spectrometer system configured to perform photometric measurements on light collected by the integrating sphere while said portions of the phosphor layer are heated by the laser and while the InGaN film is heated to the predetermined temperature.

8. The system of claim 7, further including timing electronics coupled to the laser and the probe tester to synchronize operation of the laser and the probe tester.

9. The system of claim 7, wherein the laser is positioned to direct its light through the integrating sphere onto the LED.

10. The system of claim 7, wherein the integrating sphere includes a collar configured to minimize entry of extraneous light into the integrating sphere during testing and to collect a totality of light emitted by the LED.

11. The system of claim 7, further including a moveable carrier for positioning the LED.

12. A method of performing a hot test of a light-emitting diode (LED), the LED including an indium-gallium-nitride (InGaN) film, and a phosphor layer formed on the InGaN film, the method comprising:
   using a laser to selectively heat portions of the phosphor layer to a predetermined temperature gradient;
   using an electric current source to establish a predetermined temperature in the InGaN film; and
   performing photometric measurements on the LED while the phosphor layer is heated to the predetermined temperature gradient and while the InGaN film is at the predetermined temperature.

13. The method of claim 12, wherein using the laser includes targeting excitation of silicone used as a binder in the phosphor layer.

14. The method of claim 12, wherein using the laser includes targeting excitation of active phosphor ions in the phosphor layer.

15. The method of claim 12, wherein using the laser includes using an optical light source to selectively excite vibrational modes of silicone in the phosphor layer, thereby generating a temperature gradient in the phosphor layer.

16. The method of claim 12, wherein using the laser includes using an optical light source to selectively excite vibrational modes of one of methanol and a hydrocarbon wetting agent in the phosphor layer, thereby generating a temperature gradient in the phosphor layer.

17. The method of claim 12, wherein the electric current includes applying an electric current to the InGaN film.

18. A system for hot testing of light-emitting diodes (LEDs), each LED including an indium-gallium-nitride (InGaN) film, and a phosphor layer formed on the InGaN film, the system comprising:
   a laser configured to selectively heat portions of the phosphor layer to a predetermined temperature gradient;
   an electric current source configured to establish a predetermined temperature in the InGaN film;
   an integrating sphere for positioning over the LED, the integrating sphere configured to collect light emitted by the LED during testing and
   a spectrometer system configured to perform photometric measurements on light collected by the integrating sphere while the phosphor layer is heated to the predetermined temperature gradient and while the InGaN film is at the predetermined temperature.

19. The system of claim 18, wherein the laser includes one of an optical parametric oscillator and a Cr+3 insulating crystal laser configured to excite silicone used as a binder in the phosphor layer.

20. The system of claim 18, wherein the laser includes an InGaN laser configured to excite active phosphor ions in the phosphor layer.

21. The system of claim 18, wherein the laser includes a coherent light source configured to excite active phosphor ions in the phosphor layer.

22. The system of claim 18, wherein a wavelength of coherent light generated by the laser is between 2.0 microns and 3.5 microns, and an average power of the coherent light is between 100 watts and 12 watts for selectively exciting either one of silicone and methanol dopant wetting agents of the phosphor layer.

23. The system of claim 18, wherein a wavelength of coherent light generated by the laser is between 0.45 microns and 0.53 microns, and an average power of the coherent light is between 100 watts and 12 watts.

24. The system of claim 18, further including a plurality of lasers, which in combination provide an average coherent power of 12 watts.

25. The system of claim 18, wherein the electric current includes an electrical probe tester.

26. The system of claim 18, further including a plurality of electric currents.

* * * * *